(12) United States Patent
Wu et al.

(10) Patent No.: US 11,189,030 B2
(45) Date of Patent: Nov. 30, 2021

(54) METHOD AND DEVICE FOR DETERMINING LIVER SEGMENTS IN A MEDICAL IMAGE

(71) Applicant: SHANGHAI UNITED IMAGING HEALTHCARE CO., LTD., Shanghai (CN)

(72) Inventors: Ke Wu, Shanghai (CN); Xu Wang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 234 days.

(21) Appl. No.: 16/231,709

(22) Filed: Dec. 24, 2018

(65) Prior Publication Data
US 2019/0130576 A1 May 2, 2019

Related U.S. Application Data

(63) Continuation of application No. PCT/CN2017/095332, filed on Jul. 31, 2017.

(51) Int. Cl.
*G06K 9/00* (2006.01)
*G06T 7/11* (2017.01)
(Continued)

(52) U.S. Cl.
CPC .............. *G06T 7/11* (2017.01); *A61B 5/4244* (2013.01); *G06T 7/00* (2013.01); *G06T 7/0012* (2013.01);
(Continued)

(58) Field of Classification Search
CPC ... G06T 7/11; G06T 7/00; G06T 7/143; G06T 7/136; G06T 7/0012; G06T 7/13;
(Continued)

(56) References Cited

U.S. PATENT DOCUMENTS

| 5,234,439 A | 8/1993 | Wilk et al. |
| 8,355,553 B2 * | 1/2013 | Fidrich ............... G06T 7/11 382/131 |

(Continued)

FOREIGN PATENT DOCUMENTS

| CN | 1801214 A | 7/2006 |
| CN | 102693540 A | 9/2012 |

(Continued)

OTHER PUBLICATIONS

Gerald Glombitza et al., Virtual Planning of Liver Resections: Image Processing, Visualization and Volumetric Evaluation, International Journal of Medical Informatics, 53(2-3): 225-237, 1999.
(Continued)

*Primary Examiner* — Van D Huynh
(74) *Attorney, Agent, or Firm* — Metis IP LLC

(57) ABSTRACT

The present disclosure provides methods and devices for determining liver segments in a medical image. The methods may be implemented on the devices. The method may include: obtaining a scan image; obtaining a segmentation protocol; obtaining segmentation information associated with the scan image; determining one or more marked points based on the segmentation information and the segmentation protocol; determining one or more segmentation surfaces based on the one or more marked points; and determining a segmentation result of at least part of a liver in the scan image based on the one or more segmentation surfaces.

20 Claims, 13 Drawing Sheets

(51) Int. Cl.
*G16H 30/40* (2018.01)
*G06T 7/143* (2017.01)
*G06T 7/136* (2017.01)
*G06T 7/00* (2017.01)
*A61B 5/00* (2006.01)
*G06T 7/13* (2017.01)
*A61B 5/055* (2006.01)
*A61B 6/00* (2006.01)

(52) U.S. Cl.
CPC ............... *G06T 7/13* (2017.01); *G06T 7/136* (2017.01); *G06T 7/143* (2017.01); *G16H 30/40* (2018.01); *A61B 5/055* (2013.01); *A61B 6/52* (2013.01); *A61B 2576/02* (2013.01); *G06T 2207/30056* (2013.01)

(58) Field of Classification Search
CPC ............. G06T 2207/30056; G06T 7/12; G06T 2207/10081; G06T 2207/10088; G06T 2207/10104; G16H 30/40; A61B 5/4244; A61B 2576/02; A61B 6/52; A61B 5/055
USPC .......................................................... 382/128
See application file for complete search history.

(56) References Cited

U.S. PATENT DOCUMENTS

| | | | | |
|---|---|---|---|---|
| 8,750,585 | B2* | 6/2014 | Liu | G06T 7/11 382/128 |
| 9,367,924 | B2* | 6/2016 | Gritsenko | G06T 7/174 |
| 2008/0103385 | A1* | 5/2008 | Ma | G06T 7/149 600/416 |
| 2009/0097726 | A1* | 4/2009 | Rusko | G06T 7/0012 382/131 |
| 2009/0257630 | A1* | 10/2009 | Liang | G06T 19/20 382/128 |
| 2011/0052028 | A1* | 3/2011 | Shreiber | G06T 7/11 382/131 |
| 2011/0158491 | A1* | 6/2011 | Markova | G06T 7/41 382/128 |
| 2011/0164064 | A1* | 7/2011 | Tanaka | A61B 5/103 345/667 |
| 2011/0317888 | A1* | 12/2011 | Simon | G06T 7/149 382/128 |
| 2012/0207366 | A1* | 8/2012 | Liu | G06T 7/136 382/128 |
| 2015/0063668 | A1* | 3/2015 | You | G06T 7/11 382/131 |
| 2017/0262978 | A1* | 9/2017 | Reynolds | A61B 6/032 |

FOREIGN PATENT DOCUMENTS

| | | |
|---|---|---|
| CN | 103810752 A | 5/2014 |
| CN | 104463860 A | 3/2015 |
| CN | 105574862 A | 5/2016 |
| WO | 2007053676 A2 | 5/2007 |
| WO | 2009111753 A2 | 9/2009 |

OTHER PUBLICATIONS

The Extended European Search Report in European Application No. 17919994.8 dated Jun. 26, 2020, 8 pages.
International Search Report in PCT/CN2017/095332 dated May 3, 2018, 7 Pages.

* cited by examiner

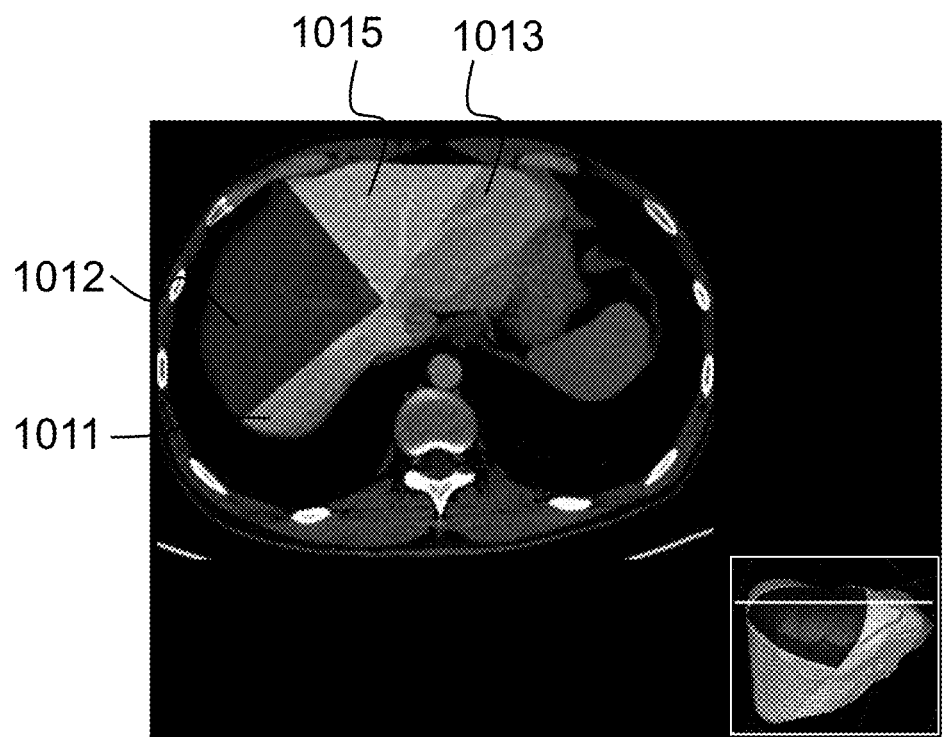
FIG. 10-A
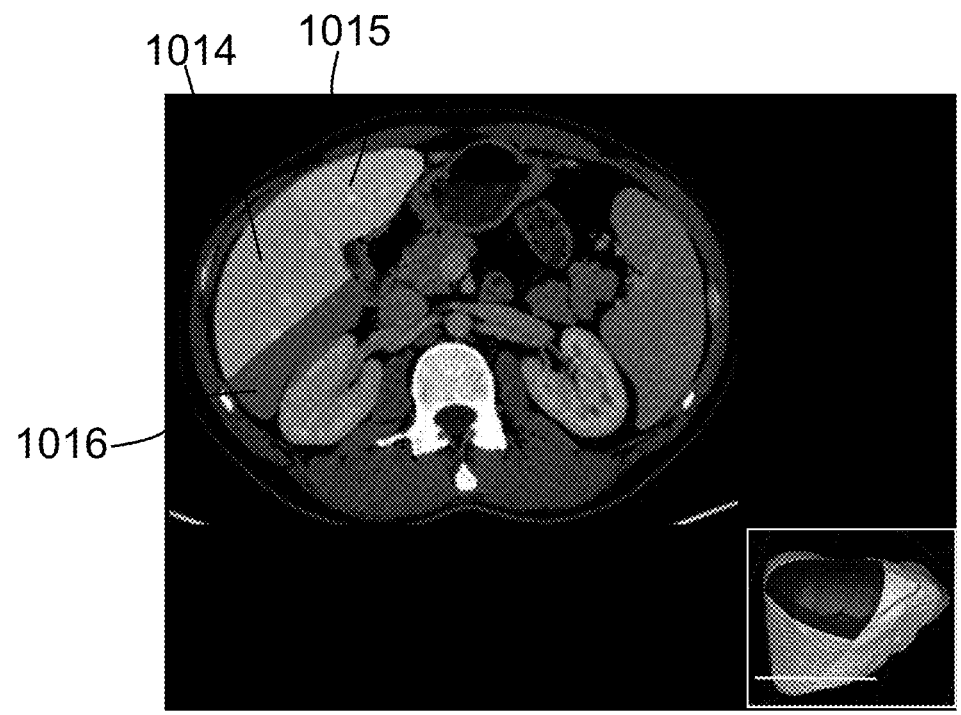
FIG. 10-B

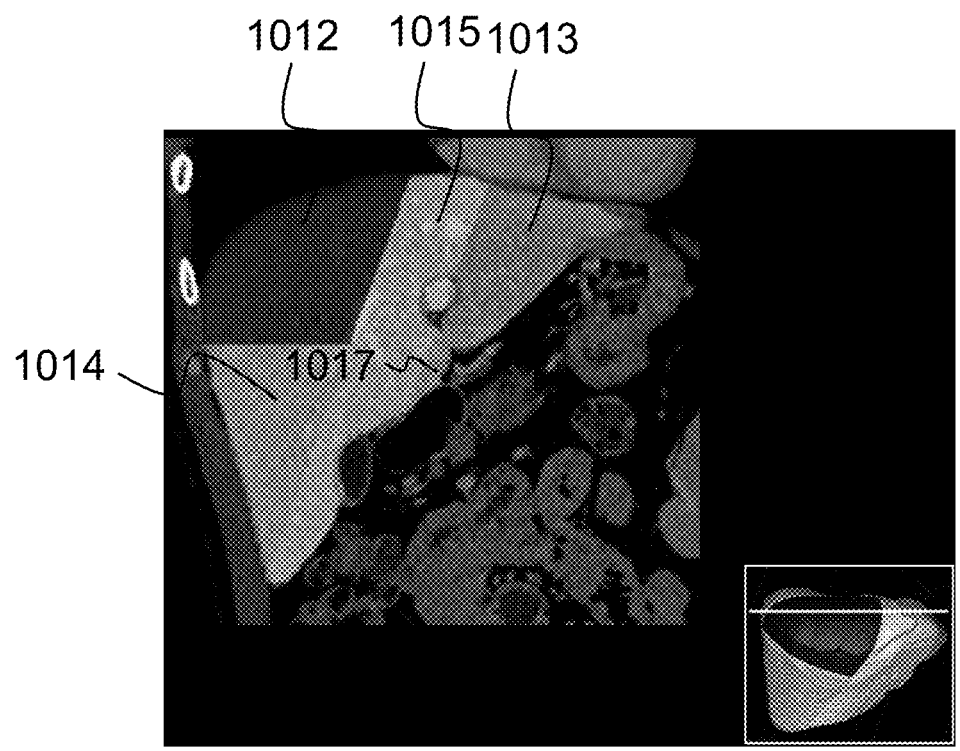
FIG. 10-C
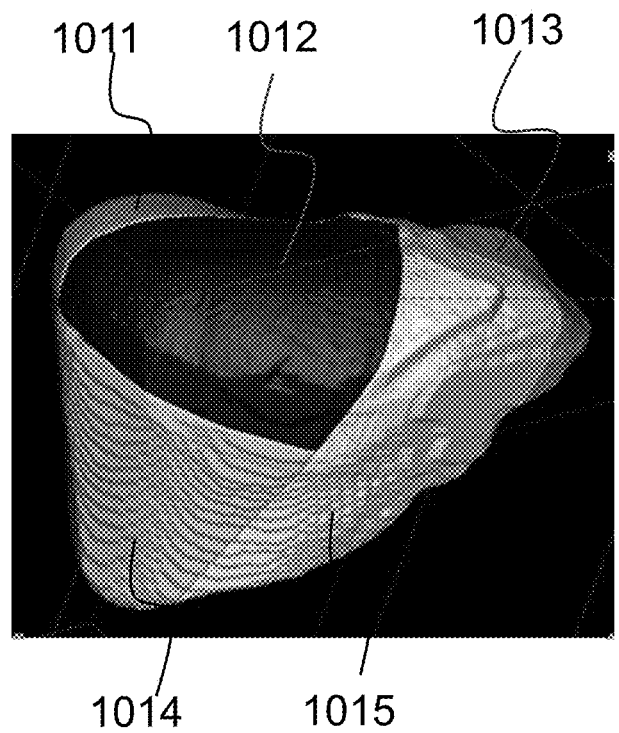
FIG. 10-D

US 11,189,030 B2

METHOD AND DEVICE FOR DETERMINING LIVER SEGMENTS IN A MEDICAL IMAGE

CROSS-REFERNCE TO RELATED APPLICATIONS

This application is a continuation of International Application No. PCT/CN2017/095332 filed on Jul. 31, 2017, the entire contents of which are hereby incorporated by reference.

TECHNICAL FIELD

The present disclosure is generally related to medical imaging, more particularly to method and device for determining liver segments in a medical image.

BACKGROUND

In the field of medical imaging, determination of liver segments is significant for describing a location of a lesion, determining a treatment plan and a resection region of a liver, and choosing an interventional therapy for a liver tumor, etc. However, existing techniques for determining liver segments in a medical image often require doctors to use a computer-aided software to segment a liver in a medical image manually. There are various problems related to determining liver segments in a medical image automatically, such as a complicated, slow, and time-consuming calculation, difficulty in determining a continuous and smooth segmentation surface, and difficulty in accommodating a plurality of segmentation protocols, etc. Therefore, it would be desirable to provide methods and devices for determining liver segments in a medical image, which may automatically determine segmentation surfaces, increase a speed of determining the segmentation surfaces, determine continuous segmentation surfaces, and accommodate a plurality of segmentation protocols for determining liver segments in a medical image.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

According to an aspect of the present disclosure, a method for determining liver segments in a medical image may include obtaining a scan image; obtaining a segmentation protocol; obtaining segmentation information associated with the scan image; determining one or more marked points based on the segmentation information and the segmentation protocol; determining one or more segmentation surfaces based on the one or more marked points; and determining a segmentation result of at least part of a liver in the scan image based on the one or more segmentation surfaces.

In some embodiments, the scan image may include a magnetic resonance imaging (MRI) image, a computed tomography (CT) image or a positron emission tomography (PET) image.

In some embodiments, the scan image may include a target object, and the target object may include the at least part of the liver.

In some embodiments, the segmentation information may include at least one of image grayscale information, image structure information, structure information of the target object, and blood vessel information of the target object.

In some embodiments, the segmentation protocol may include at least one of segmentation relating to a hepatic left lobe and a hepatic right lobe, segmentation relating to hepatic left three lobes, segmentation relating to hepatic right three lobes, segmentation relating to a hepatic middle lobe, segmentation relating to an upper segment and a lower segment of the hepatic right lobe, segmentation relating to hepatic four lobes, segmentation relating to hepatic five segments, segmentation relating to hepatic six segments, segmentation relating to hepatic seven segments, or segmentation relating to hepatic eight segments.

In some embodiments, the one or more marked points may include at least one of a point on a hepatic portal, a venous intersection point, a point on a middle hepatic vein, a point on a right hepatic vein, a hepatic fissure point, a fork on a left branch of a portal vein, a fork on a right branch of a portal vein, or a small hepatic fissure point of liver left lobe.

In some embodiments, the determining of the one or more marked points based on the segmentation information and the segmentation protocol may include: for the segmentation relating to the hepatic left lobe and the hepatic right lobe, determining the point on the hepatic portal, the venous intersection point, and the point on the middle hepatic vein; for the segmentation relating to the hepatic left three lobes, determining at least one of the point on the hepatic portal, the venous intersection point, the point on the right hepatic vein, or the point on the middle hepatic vein; for the segmentation relating to the hepatic right three lobes, determining at least one of the point on the hepatic portal, the venous intersection point, the hepatic fissure point, the fork on the left branch of the portal vein, or the point on the middle hepatic vein; for the segmentation relating to the hepatic middle lobe, determining at least one of the point on the hepatic portal, the venous intersection point, the hepatic fissure point, the fork on the left branch of the portal vein, the point on the right hepatic vein, or the point on the middle hepatic vein; for the segmentation relating to the upper segment and the lower segment of the hepatic right lobe, determining the point on the hepatic portal, the venous intersection point, the fork on the right branch of the portal vein, and the point on the middle hepatic vein; for the segmentation relating to the hepatic four lobes, determining the point on the hepatic portal, the venous intersection point, the hepatic fissure point, the fork on the left branch of the portal vein, the point on the right hepatic vein, and the point on the middle hepatic vein; for the segmentation relating to the hepatic five segments, determining the point on the hepatic portal, the venous intersection point, the hepatic fissure point, the fork on the left branch of the portal vein, the point on the right hepatic vein, and the point on the middle hepatic vein; for the segmentation relating to the hepatic six segments, determining the point on the hepatic portal, the venous intersection point, the hepatic fissure point, the fork on the left branch of the portal vein, the point on the right hepatic vein, the fork on the right branch of the portal vein, and the point on the middle hepatic vein; for the segmentation relating to the hepatic seven segments, determining the point on the hepatic portal, the venous intersection point, the hepatic fissure point, the fork on the left branch of the portal vein, the point on the right hepatic vein, the fork on the right branch of the portal vein, and the point on the middle hepatic vein; and for the segmentation relating to the hepatic eight segments, determining the point on the hepatic portal, the venous intersection point, the hepatic fissure point, the fork on the left branch of the portal vein, the point on the right hepatic vein, the fork on the right branch of the portal vein, the point on the middle hepatic vein, and the small hepatic fissure point of the hepatic left lobe.

In some embodiments, the determining of the one or more marked points may include determining the one or more marked points based on a vascular tracking algorithm.

In some embodiments, the one or more marked points may be determined automatically.

In some embodiments, the determining of the one or more marked points may include: determining one or more candidate marked points; obtaining a user instruction, the user instruction including at least one of adjusting the position of the one or more candidate marked points, deleting at least one of the one or more candidate marked points, and adding one or more new candidate marked points; and determining the one or more marked points based on the user instruction and the one or more candidate marked points.

In some embodiments, the one or more segmentation surfaces may include at least one of a segmentation flat surface and a segmentation curved surface.

In some embodiments, the determining of the one or more segmentation surfaces may include determining the segmentation curved surface, which may include: obtaining cross sections based on the scan image; determining one or more segmentation flat surfaces based on the one or more marked points; determining lines of intersection based on the one or more segmentation flat surfaces and the cross sections; and determining the segmentation curved surface based on the lines of intersection.

In some embodiments, the determining of the lines of intersection may include: determining first lines of intersection based on the one or more segmentation flat surfaces and the cross sections; and determining second lines of intersection based on the first lines of intersection using an interpolation algorithm.

In some embodiments, the method may further include determining a liver surgery plan based on the segmentation result of the at least part of the liver in the scan image.

According to another aspect of the present disclosure, a method for determining liver segments in a medical image may include obtaining a scan image; obtaining a segmentation protocol; determining at least part of a liver and blood vessel information associated with the scan image by automatically segmenting the scan image based on the segmentation protocol; automatically determining one or more marked points on the liver based on the blood vessel information; automatically determining one or more segmentation surfaces based on the one or more marked points; and determining a segmentation result of the at least part of the liver in the scan image by segmenting the at least part of the liver based on the one or more segmentation surfaces.

According to yet another aspect of the present disclosure, a device for determining liver segments in a medical image. The device may include: a computer-readable storage medium, configured to store executable modules; and a processor executing the executable module stored in the computer readable storage medium. The executable modules may include an image acquisition module, configured to acquire a scan image; a segmentation protocol acquisition module, configured to acquire a segmentation protocol; a segmentation information acquisition module, configured to acquire segmentation information; and a segmentation module, configured to: automatically determine one or more marked points based on the segmentation information and the segmentation protocol; automatically determine one or more segmentation surfaces based on the one or more marked points; and determine a segmentation result of at least part of a liver in the scan image based on the one or more segmentation surfaces.

BRIEF DESCRIPTION OF THE DRAWING

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIGS. 10-A to 10-D are schematic diagrams illustrating exemplary segmentation results of a liver in a scan image according to some embodiments of the present disclosure;

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

Figure 1:
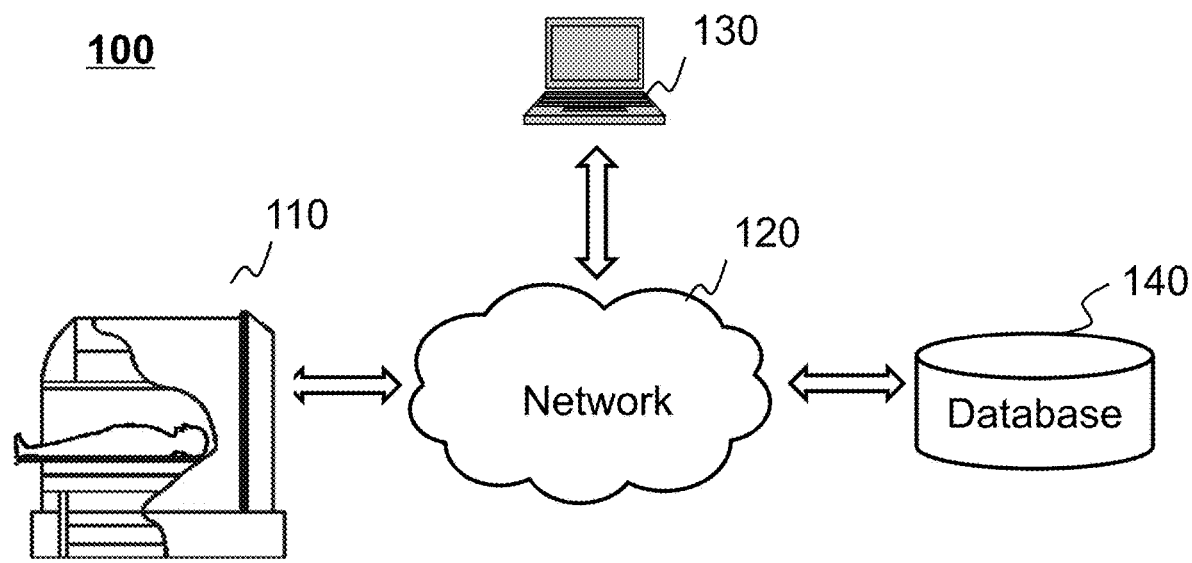
FIG. 1 is a schematic diagram illustrating an exemplary liver segment determination system according to some embodiments of the present disclosure.

FIG. 1 is a schematic diagram illustrating an exemplary liver segment determination system according to some embodiments of the present disclosure. Image segmentation may refer to a process of dividing an image into different regions based on certain criterions. Liver segment determination may refer to a process of dividing a liver in an image into different regions based on certain criterions. The liver segment determination is significant for describing a location of a lesion, determining a treatment plan and a resection region of a liver, and choosing an interventional therapy for a liver tumor, etc.

The liver segment determination system 100 may include one or more imaging devices 110, one or more networks 120, one or more processing devices 130, and one or more databases 140.

The imaging device 110 may obtain scan data by scanning a subject. The scan data may be sent to the processing device 130 via the network 120 for further processing, and may also be stored in the database 140. The subject may include a human body, an animal, etc. The imaging device 110 may include but is not limited to a Computed Tomography (CT) device, a Magnetic Resonance Imaging (MRI) device or a Positron Emission Computed Tomography (PET) device.

The network 120 may be a single network or a combination of a plurality of networks. The network 120 may include, but is not limited to, a local area network, a wide area network, a public network, a wireless local area network, a virtual network, a metropolitan area network, a public switched telephone network, or the like, or any combination thereof. The network 120 may include a plurality of network access points, for example, a wire access point or a wireless access points, a base station switching point or a network switching point, through which one or more components of the liver segment determination system 100 may be connected to the network 120 to exchange data and/or information.

The processing device 130 may generate a processing result by processing and/or analyzing the input data (e.g., the scan data, and/or a scan image obtained from the processing device 130 and/or the database 140). For example, the processing device 130 may generate a scan image based on the scan data. As another example, the processing device 130 may segment a liver in a scan image to obtain a segmentation result of the liver. The scan image may be a two-dimensional (2D) image or a three-dimensional (3D) image. The processing device 130 may include a processor and an input/output (I/O) device (not shown in FIG. 1). In some embodiments, the processor may be a server, and a server group. The server group may be a centralized group, such as a data center. The server group may also be a distributed group, such as a distributed system. The processor may include a cloud server, a file server, a database server, a File Transfer Protocol (FTP) server, an application server, a proxy server, a mail server, or the like, or any combination thereof. The server may be a local server or a remote server. For example, the server may access information and/or data stored in the imaging device 110, and/or the database 140 via the network 120. As another example, the server may be directly connected to the imaging device 110, and/or the database 140 to access stored information and/or data. In some embodiments, the server may access information stored in the database 140 (e.g., medical images stored in the database 140), and information obtained from the imaging device 110 (e.g., the scan data obtained from the imaging device 110).

In some embodiments, the I/O device may input data to the processor, and receive data output from the processor. The I/O device may show the output data in forms of numbers, characters, images, sounds, etc. In some embodiments, the I/O device may include, but is not limited to, an input device and/or an output device. The input device may include, but is not limited to, a character input device (e.g., a keyboard), an optical reading device (e.g., an optical mark reader, an optical character reader), a graphical input device (e.g., a mouse, an operating rod, a light pen), an image input device (e.g., a camera, a scanner, a facsimile apparatus), an analog input device (e.g., a language analog-to-digital conversion identification system), or the like, or any combination thereof. The output device may include, but is not limited to, a display device, a print device, a graphic plotter, an image output device, a voice output device, a magnetic recording system, or the like, or any combination thereof. In some embodiments, the processing device 130 may further include a storage device (not shown in FIG. 1). The storage device may store information, for example, programs and data, etc. In some embodiments, intermediate data and/or a processing result (e.g., a scan image, a segmentation result of a liver, etc.) generated by the processing device 130 may be stored in the database 140 and/or the storage device of the processing device 130, or may be output by the I/O device.

The database 140 may include any device with a function of storing. The database 140 may store scan data collected from the imaging device 110 and/or data generated from the processing device 130. The database 140 may be local or remote. The database 140 may include, but is not limited to, a hierarchical database, a network database, a relational database, or the like, or any combination thereof. The database 140 may digitize information and store the digitized information in an electric storage device, a magnetic storage device, an optical storage device, etc. The database 140 may store various information, such as procedures, data, etc. The database 140 may be a device that stores information using electric energy, such as a memorizer, a random access memory (RAM), a read only memory (ROM), or the like, or a combination thereof. The RAM may include a dekatron, a selectron, a delay line memory, a Williams tube, a dynamic random access memory (DRAM), a static random access memory (SRAM), a thyristor random access memory (T-RAM), a zero capacitor random access memory (Z-RAM), or the like, or a combination thereof. The ROM may include a read-only memory bubble memory, a magnetic button line memory, a memory thin film, a magnetic plate line memory, a core memory, a magnetic drum memory, a CD-ROM drive, a hard disk, a magnetic tape, an early nonvolatile memory (the NVRAM), a phase change memory, a magnetoresistive random access memory modules, a ferroelectric random access memory, a nonvolatile SRAM, a flash memory, a type of electronic erasing rewritable read-only memory, an erasable programmable read-only memory, a programmable read-only memory, a mask ROM, a floating connecting doors random access memory, a nanometer random access memory, a racetrack memory, a variable resistive memory, a programmable metallization cell, or the like, or a combination thereof. The database 140 may be a device that stores information using magnetic energy, such as a hard disk, a floppy disk, a magnetic tape, a magnetic core memory, a bubble memory, a U disk, a flash memory, or the like, or a combination thereof. The database 140 may be a device that stores information using optics energy, such as a CD, a DVD, or the like, or a combination thereof. The database 140 may be a device that stores information using magnetic-optics energy, such as a magneto-optical disk. The database 140 may store information in, for example, a random storage mode, a serial access storage mode, a read-only storage mode, or the like, or a combination thereof. In some embodiments, the database 140 may be a non-permanent memory, a permanent memory, or a combination thereof. It should be noted that the above description of storage devices is provided for the purpose of illustration, and not intended to limit the scope of the present disclosure.

It should be noted that the above description is merely provided for the purposes of illustration, and not intended to limit the scope of the present disclosure. Many alternatives, modifications, and variations will be apparent to those skilled in the art. The features, structures, methods, and other features of the exemplary embodiments described herein may be combined in various ways to obtain additional and/or alternative exemplary embodiments. For example, the database 140 may be a cloud computing platform including a public cloud, a private cloud, a community and hybrid cloud, etc. However, those variations and modifications do not depart the scope of the present disclosure.

Figure 2:
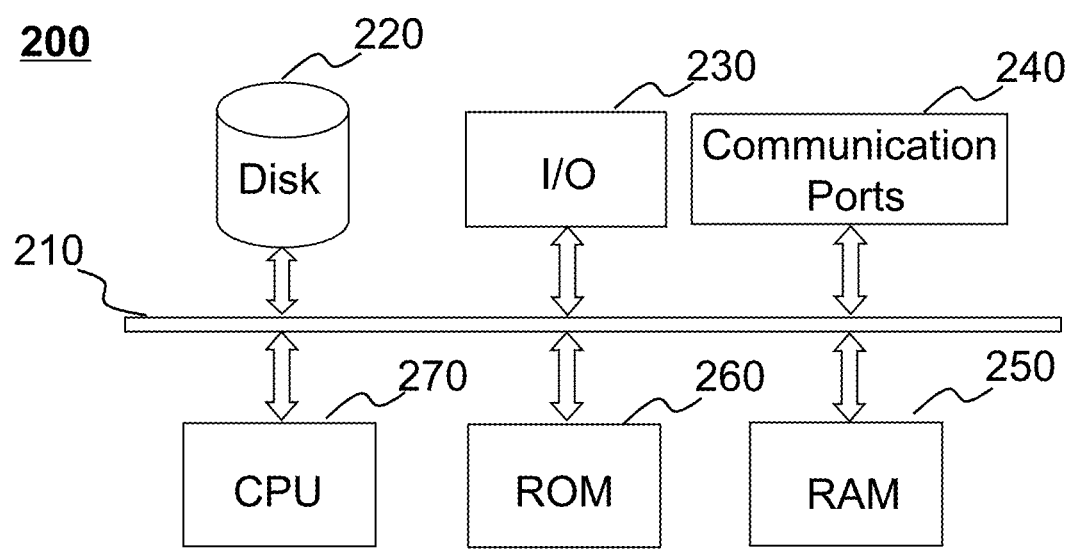
FIG. 2 is a schematic diagram illustrating exemplary hardware and/or software components of a computing device according to some embodiments of the present disclosure.

FIG. 2 is a schematic diagram illustrating exemplary hardware and/or software components of a computing device according to some embodiments of the present disclosure. The computer may be a general-purpose computer, or a computer with a specific purpose. The processing device 130 may be implemented on the computing device 200, via its hardware, software program, firmware, or a combination thereof. Although only one such computer is shown for convenience, the computer functions related to the processing device 130 as described herein may be implemented in a distributed manner on a number of similar platforms to distribute the processing load.

The computing device 200, for example, may include COM ports 240 connected to and from a network connected thereto to facilitate data communications. The computing device 200 may also include a central processing unit (CPU) 270, in the form of one or more processors, for executing program instructions. The exemplary computer platform may include an internal communication bus 210, program storage and data storage of different forms, for example, a disk 220, and a read only memory (ROM) 260, or a random access memory (RAM) 250, for various data files to be processed and/or transmitted by the computer, and program instructions to be executed by the CPU 270. The methods and/or processes of the present disclosure may be implemented as the program instructions. The computing device 200 may also include an I/O 230, supporting input/output between the computer and other components therein. The computing device 200 may also receive programming and data via network communications.

Figure 3:
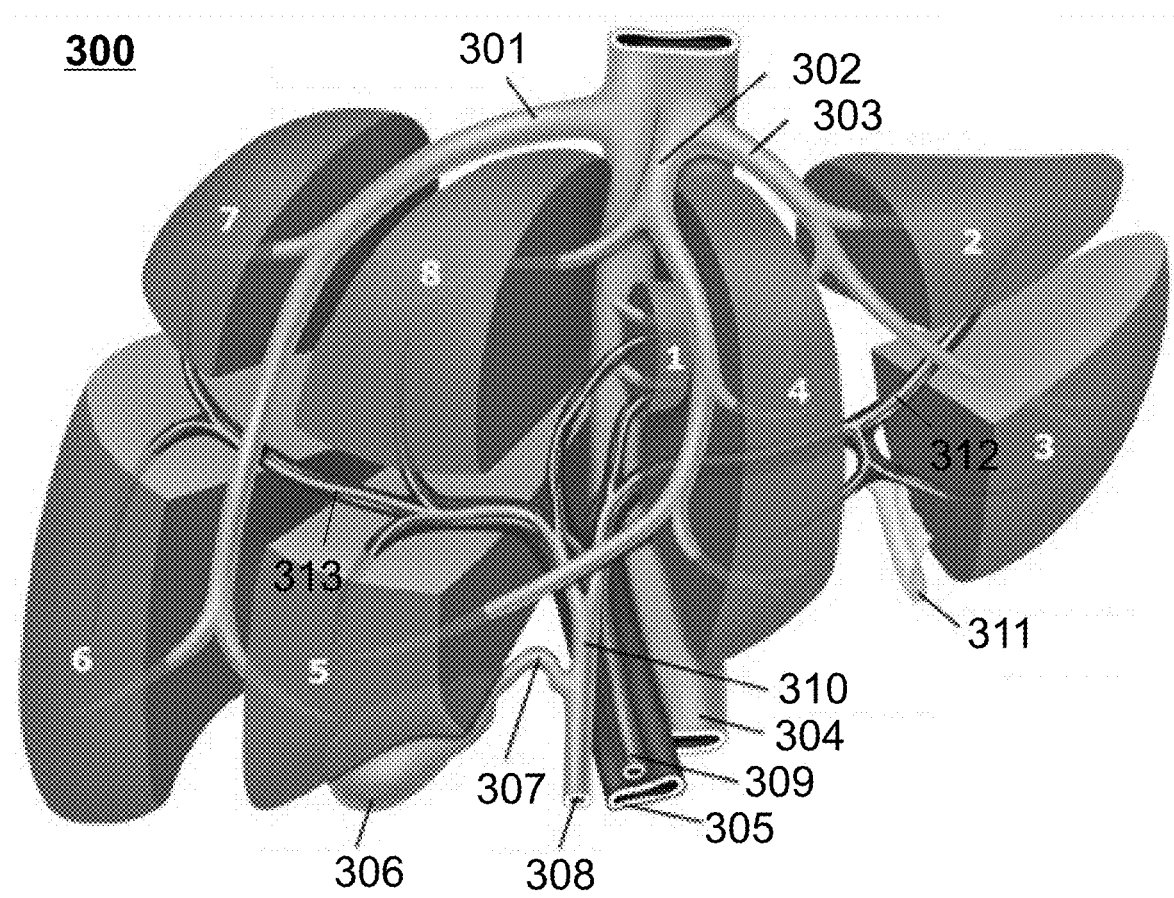
FIG. 3 is a schematic diagram illustrating an exemplary Couinaud segmentation model of determining liver segments according to some embodiments of the present disclosure.

FIG. 3 is a schematic diagram illustrating an exemplary Couinaud segmentation model of determining liver segments according to some embodiments of the present disclosure. A segmentation module of determining liver segments may define liver segments of a liver. The segmentation model of determining liver segments may include but is not limited to a Couinaud segmentation model, a segmentation model based on the structure of liver surface, or a Couinaud segmentation model modified by Bismuth, etc. The Couinaud segmentation model may divide a liver into eight regions according to the distribution of blood vessels in the liver. The Couinaud segmentation model modified by Bismuth may divide a liver into nine regions based on the Couinaud segmentation model. The segmentation model based on the structure of liver surface may divide a liver into four regions: a left lobe, a right lobe, a quadrate lobe, and a caudate lobe. The structure of a liver may be shown in FIG. 3. As shown in FIG. 3, 301 may represent a right hepatic vein, 302 may represent a middle hepatic vein, 303 may represent a left hepatic vein, 304 may represent an inferior vena cava, 305 may represent a hepatic portal vein, 306 may represent a gallbladder, 307 may represent a cystic duct, 308 may represent a bile duct, 309 may represent a hepatic artery, 310 may represent a hepatic duct, and 311 may represent a ligamentum teres hepatis. The hepatic portal vein 305 may include a left branch 312 and a right branch 313. The hepatic vein may include the right hepatic vein 301, the middle hepatic vein 302, and the left hepatic vein 303.

In some embodiments, the Couinaud segmentation model may segment a liver into a plurality of regions based on functions of the liver. The plurality of regions may be independent to each other. At least one of the plurality of regions could be resected without damaging the other regions. The plurality of regions may be referred to as liver segments. In some embodiments, the Couinaud segmentation model may divide a liver into eight independent liver segments based on the distribution of the hepatic portal vein 305 and the hepatic vein. Each liver segment may has its own input blood vessels, output blood vessels, and bile duct. Particularly, each liver segment may include branches of the hepatic portal vein 305, the hepatic artery 309, and the bile duct 308. Each liver segment may be surrounded by output blood vessels flowing through the hepatic vein. In some embodiments, the eight liver segments may be referred to as standard liver segments. The standard liver segments may be numbered using Arabic or Roman numerals in a clockwise order from small to large, for example, liver segment 1, liver segment 2, liver segment 3, liver segment 4, liver segment 5, liver segment 6, liver segment 7, and liver segment 8 (as shown in FIG. 3), or liver segment I, liver segment II, liver segment III, liver segment IV, liver segment V, liver segment VI, liver segment VII, and liver segment VIII.

In some embodiments, according to the Couinaud segmentation model, the middle hepatic vein 302 may segment a liver into a left lobe (also referred to as a left liver, which may include liver segment 2, liver segment 3, and liver segment 4) and a right lobe (also referred to as a right liver, which may include liver segment 5, liver segment 6, liver segment 7, and liver segment 8). The right hepatic vein 301 may segment the right lobe into a right anterior lobe (including liver segment 5 and liver segment 8) and a right posterior lobe (including liver segment 6 and liver segment 7). The left hepatic vein 303 may segment the left lobe into a left medial lobe (liver segment 4) and a left lateral lobe (including liver segment 2 and liver segment 3). The hepatic portal vein 305 may segment a liver into an upper segment and a lower segment. The left branch 312 of the hepatic portal vein 305 may segment the left lateral lobe into an upper segment (liver segment 2) and a lower segment (liver segment 3). The right branch 313 of the hepatic portal vein 305 may segment the right anterior lobe into an upper segment (liver segment 8) and a lower segment (liver segment 5). The right branch 313 of the hepatic portal vein 305 may segment the right posterior lobe into an upper segment (liver segment 7) and a lower segment (liver segment 6). A region between the inferior vena cava 304 and the hepatic portal vein 305, which locates on the back of a liver, may be referred to as a caudate lobe (liver segment 1).

The method for determining liver segments described in the present disclosure may segment a liver in a scan image based on the Couinaud segmentation model.

Figure 4:
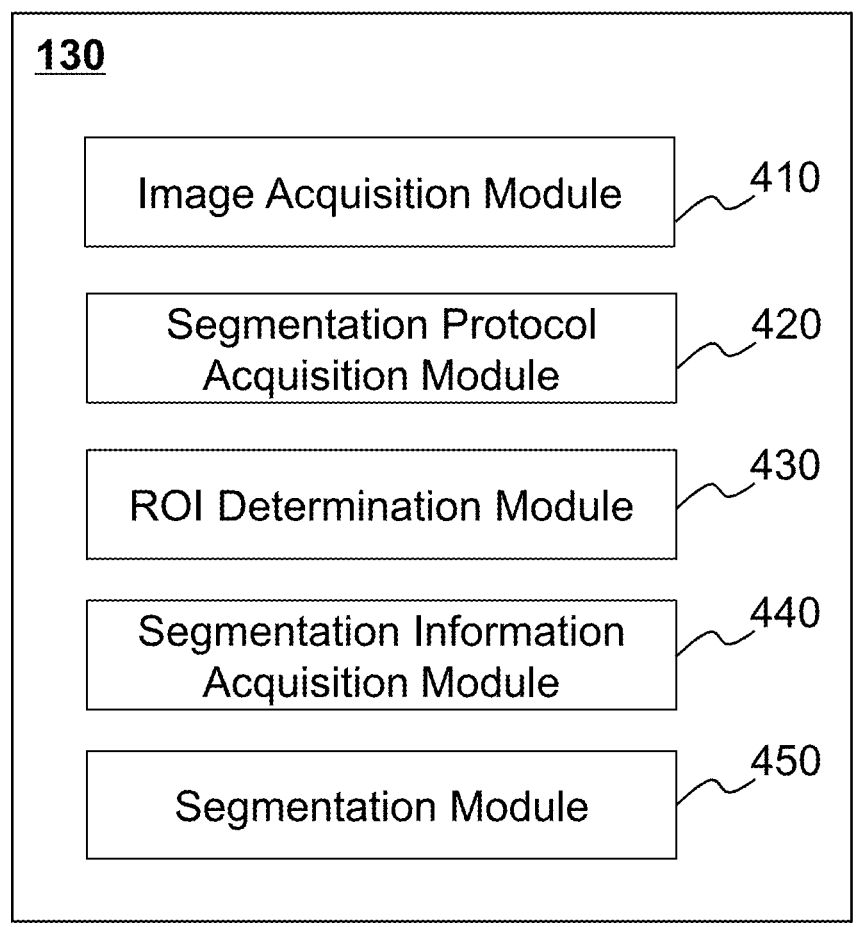
FIG. 4 is a block diagram illustrating an exemplary processing device according to some embodiments of the present disclosure.

FIG. 4 is a block diagram illustrating an exemplary processing device according to some embodiments of the present disclosure. The processing device 130 may include an image acquisition module 410, a segmentation protocol acquisition module 420, a region of interest (ROI) determination module 430, a segmentation information acquisition module 440, and a segmentation module 450. The modules described in FIG. 4 may be implemented by the CPU 270 of the computing device 200 as shown in FIG. 2. The modules may be directly (and/or indirectly) connected to each other. It should be noted that the processing device 130 described in FIG. 4 is merely provided for purpose of illustration, and not intended limit the scope of the application in said embodiments. It is understood for persons having ordinary skills in the art, multiple variations and modifications of the description of the processing device 130 in application field and details may be made under the teachings of the present disclosure based on the mechanism. For example, two of the modules may be combined as a single module, or one of the modules may be divided into two or more modules.

The image acquisition module 410 may obtain a scan image. The obtained scan image may include, but is not limited to, a CT image, an MRI image, or a PET image. The scan image may be a 2D image or a 3D image. The scan image may include, but is not limited to, an original image and/or a processed image. The original image may refer to an image obtained directly based on the scan data. The processed image may refer to an image obtained by processing the original image. The processing of the original image may include, but is not limited to, image enhancement, image recombination, 3D reconstruction, image filtering, image coding (e.g., compression coding), image format conversion, image rendering, image scaling, or the like, or any combination thereof In some embodiments, the scan image may include a target object. The target object may be an object to be segmented. The target object may include a liver or a portion of the liver. For example, for a CT image, the scan image may be a scan image of a certain section of a liver. In some embodiments, the image acquisition module 410 may obtain scan images of different sections of a liver.

In some embodiments, the image acquisition module 410 may obtain the scan data from the imaging device 110, and generate an original image based on the scan data. In some embodiments, the image acquisition module 410 may process the original image to obtain a processed image. In some embodiments, the image acquisition module 410 may obtain the original image and/or the processed image from a storage apparatus (e.g., the database 140). In some embodiments, the original image obtained by reconstructing the scan data and/or the processed image obtained by processing the original image SOmay be stored in a storage apparatus (e.g., the database 140, a storage device in the processing device 130), or may be sent to other modules for further processing (e.g. sent to the ROI determination module 430 to determine an ROI or sent to the segmentation information acquisition module 440 to obtain segmentation information).

The segmentation protocol acquisition module 420 may obtain one or more segmentation protocols. In some embodiments, the segmentation protocol may be used to determine how to segment a liver in the scan image. In some embodiments, the segmentation protocol may include, but is not limited to, segmentation relating to a hepatic left lobe and a hepatic right lobe, segmentation relating to hepatic left three lobes, segmentation relating to hepatic right three lobes, segmentation relating to a hepatic middle lobe, segmentation relating to an upper segment and a lower segment of the hepatic right lobe, segmentation relating to hepatic four lobes, segmentation relating to hepatic five segments, segmentation relating to hepatic six segments, segmentation relating to hepatic seven segments, segmentation relating to hepatic eight segments, or the like, or any combination thereof.

The segmentation relating to the hepatic left lobe and the hepatic left right may refer to segmentation for segmenting a liver into a left lobe and a right lobe. The segmentation relating to the hepatic left three lobes may refer to segmentation for segmenting a liver into left three lobes and a right posterior lobe, wherein the hepatic left three lobes may include a right anterior lobe and a left lobe. The segmentation relating to the hepatic right three lobes may refer to segmentation for segmenting a liver into right three lobes and a left lateral lobe, wherein the right three lobes may include a right lobe and a left medial lobe (liver segment 4). The segmentation relating to the hepatic middle lobe may refer to segmentation for segmenting a liver into a middle lobe, a right posterior lobe, and a left lateral lobe, wherein the middle lobe may include a left medial segment (liver segment 4) and a right anterior lobe. The segmentation relating to the upper segment and the lower segment of the hepatic right lobe may refer to segmentation for segmenting a liver into a left lobe, an upper segment of a right lobe, and a lower segment of a right lobe, wherein the upper segment of the right lobe may include an upper segment of a right anterior lobe (liver segment 8) and an upper segment of a right posterior lobe (liver segment 7), and the lower segment of the right lobe may include a lower segment of the right anterior lobe (liver segment 5) and a lower segment of the right posterior lobe (liver segment 6). The segmentation relating to the hepatic four lobes may refer to segmentation for segmenting a liver into a right anterior lobe, a right posterior lobe, a left lateral lobe, and a left medial lobe (liver segment 4). The segmentation relating to the hepatic five segments may refer to segmentation for segmenting a liver into a right anterior lobe, a right posterior lobe, a left medial lobe (liver segment 4), an upper segment of a left lateral lobe (liver segment 2), and a lower segment of the left lateral lobe (liver segment 3). The segmentation relating to the hepatic six segments may refer to segmentation for segmenting a liver into a left lateral lobe, a left medial lobe (liver segment 4), an upper segment of a right anterior lobe (liver segment 8), a lower segment of the right anterior lobe (liver segment 5), an upper segment of a right posterior lobe (liver segment 7), and a lower segment of the right posterior lobe (liver segment 6). The segmentation relating to the hepatic seven segments may refer to segmentation for segmenting a liver into an upper segment of a left lateral lobe (liver segment 2), a lower segment of the left lateral lobe (liver segment 3), a left medial lobe (liver segment 4), an upper segment of a right anterior lobe (liver segment 8), a lower segment of the right anterior lobe (liver segment 5), an upper segment of a right posterior lobe (liver segment 7), and a lower segment of the right posterior segment (liver segment 6). The segmentation relating to the hepatic eight segments may refer to segmentation for segmenting a liver into an upper segment of a left lateral lobe (liver segment 2), a lower segment of the left lateral lobe (liver segment 3), a left medial lobe (liver segment 4), an upper segment of a right anterior lobe (liver segment 8), a lower segment of the right anterior lobe (liver segment 5), an upper segment of a right posterior lobe (liver segment 7), a lower segment of the right posterior segment (liver segment 6), and a caudate lobe (liver segment 1).

In some embodiments, the segmentation protocol may be automatically obtained by the segmentation protocol acquisition module 420 from a storage apparatus (e.g., the database 140 or a storage device of the processing device 130), or may be input by a user (e.g., a doctor or an imaging technician) through an I/O device in the processing device 130, or may be obtained by the segmentation protocol acquisition module 420 from any external resource via the network 120. In some embodiments, a user (e.g., a doctor or an imaging technician) may directly input the segmentation protocol through an I/O device. For example, the user (e.g., a doctor or an imaging technician) may input the segmentation protocol through text input, voice input, etc. In some embodiments, a user (e.g., a doctor or an imaging technician) may select one or more of the segmentation protocols provided by the processing device 130.

The ROI determination module 430 may obtain an ROI based on the scan image. The ROI may include but is not limited to a target object. In some embodiments, the ROI determination module 430 may obtain the ROI automatically. In some embodiments, a user (e.g., a doctor or an imaging technician) may determine the ROI manually. Instructions relating to determining the ROI may be sent to the ROI determination module 430 through the I/O device in the processing device 130. The ROI determination module 430 may determine the ROI based on the received instructions.

The segmentation information acquisition module 440 may obtain segmentation information. The segmentation information may include, but is not limited to, image information and/or ROI information. The image information may include but not limited to image grayscale information and/or image structure information. The image grayscale information may include, but is not limited to, image data matrix, image spectrum, image 2D histogram, or the like, or any combination thereof. In some embodiments, the image spectrum may be obtained based on image transformation. The image transformation may include, but is not limited to, Fourier transformation, sine transformation (e.g., discrete cosine transformation), cosine transformation, Gabor transformation, wavelet transformation, or the like, or any combination thereof. The image structure information may include, but is not limited to, image corner information, image gradient information, image structure tensor information, image curvature, or the like, or any combination thereof.

In some embodiments, the ROI information may include, but is not limited to, structure information of a target object and/or blood vessel information of a target object. In some embodiments, the structure information may include structure information of a liver. The structure information of a liver may refer to information related to liver composition and liver surface morphology. For example, the structure information of a liver may include, but is not limited to, location information of the hepatic duct 310, the ligamentum teres hepatis 311, falciform ligament (not shown in the drawings), grooves of hepatic surface (e.g., a hepatic left longitudinal groove), fossae of hepatic surface (e.g., a gallbladder fossa), fissures of hepatic surface (e.g., a middle hepatic fissure), or the like, or any combination thereof. The blood vessel information of a target object may include blood vessel information of a liver. The blood vessel information of a liver may refer to information related to the distribution of blood vessels in the liver. For example, blood vessel information of a liver may include, but is not limited to, vascular contour information and/or vascular location information. The vascular contour information may include, but is not limited to, locations of the right hepatic vein 301, the middle hepatic vein 302, the left hepatic vein 303, the inferior vena cava 304, the hepatic portal vein 305, or the hepatic artery 309 in the liver, vascular intersections (e.g., an intersection of the right hepatic vein 301, the middle hepatic vein 302, the left hepatic vein 303, and the inferior vena cava 304), morphological information of blood vessels (e.g., the hepatic portal vein 305 may include the left branch 312 and the right branch 313, locations of forks on the hepatic portal vein 305, locations of forks on the left branch 312 of the hepatic portal vein 305 and/or the right branch 313 of hepatic portal vein 305).

The segmentation module 450 may segment a target object in the scan image. In some embodiments, the segmentation module 450 may segment the target object in the scan image based on the segmentation information and the segmentation protocol. In some embodiments, the segmentation module 450 may segment a liver based on the structure information of the liver and/or the blood vessel information of the liver. For example, the segmentation module 450 may segment a liver into a hepatic left lobe and a hepatic right lobe based on the position of the falciform ligament in the liver. As another example, the segmentation module 450 may segment a liver based on the distribution of blood vessels in the liver. As still another example, the segmentation module 450 may segment a liver based on the distribution of blood vessels and the surface morphology (e.g., the position of the gallbladder fossa and the liver fissure in the liver) of the liver.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the ROI determination module 430 may be omitted, or be integrated into other modules of the processing device 130. As another example, the processing device 130 may further include a storage module (not shown in FIG. 4). The storage module may be configured to store data generated during any process performed by any component of in the processing device 130. As still another example, each of components of the processing device 130 may correspond to a storage module, respectively. Additionally or alternatively, the components of the processing device 130 may share a common storage module.

Figure 5:
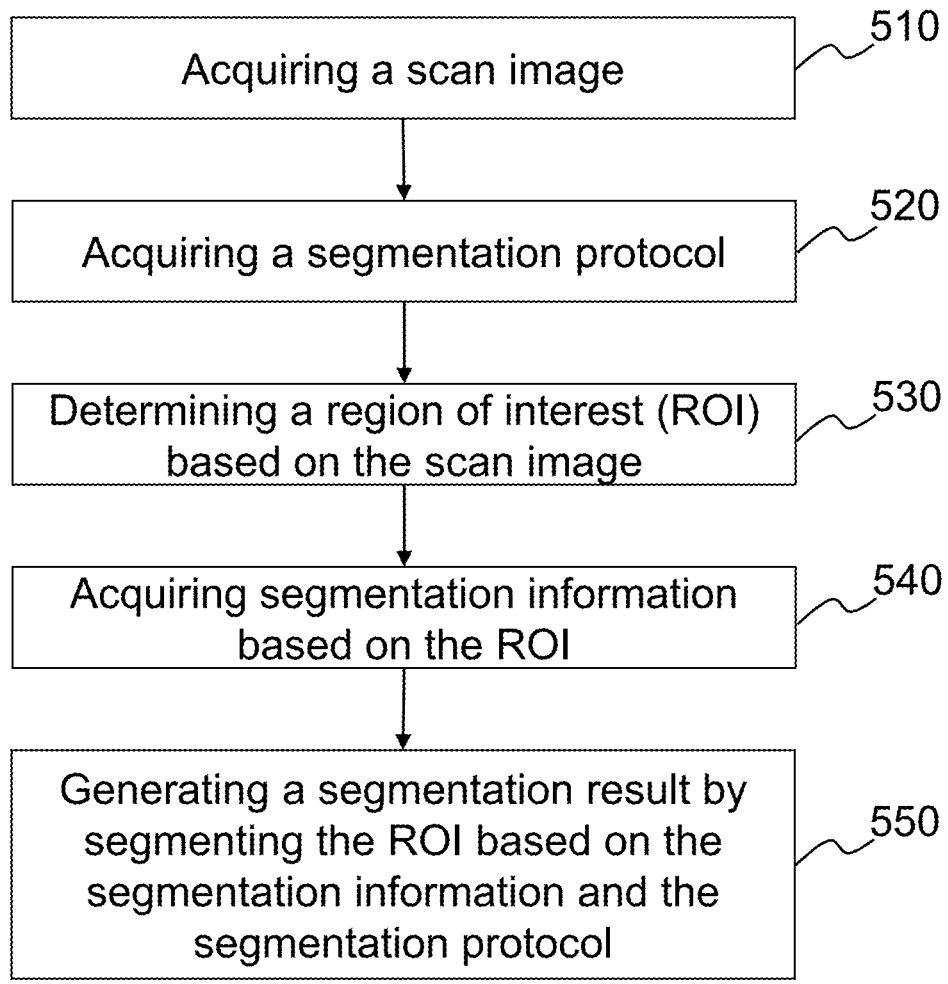
FIG. 5 is a flowchart illustrating an exemplary process for determining liver segments in a medical image according to some embodiments of the present disclosure.

FIG. 5 is a flowchart illustrating an exemplary process for determining liver segments in a medical image according to some embodiments of the present disclosure.

In 510, the image acquisition module 410 may obtain a scan image. The obtained scan image may include a CT image, an MRI image, or a PET image. The scan image may be a 2D image or a 3D image. The scan image may include but is not limited to an original image or a processed image. The original image may be obtained directly based on the scan data. The processed image may be obtained by processing the original image. The processing of the original image may include, but is not limited to, image enhancement, image recombination, 3D reconstruction, image filtering, image coding (e.g., compression coding), image format conversion, image rendering, image scaling, or the like, or any combination thereof.

The image enhancement may increase the contrast of the whole or part of an image. For example, in a CT image of a human peritoneal cavity, the contrast of a particular organ (e.g., a liver) may be increased relative to other organs, which may make a user (e.g., a doctor or an imaging technician) quickly identify the particular organ. The image recombination may generate an image of any section of the target object based on the images that have been generated. For example, for a CT image, the image acquisition module 410 may generate, based on a 2D image (e.g., an original image) of a cross section of a liver, images of other sections of the liver (e.g., an image of a coronal plane and an image of a sagittal plane) by the image recombination. The cross section may refer to a plane that is parallel to the ground and divides the target object into an upper part and a lower part. The sagittal plane may refer to a plane that is vertical to the ground and divides the target object into a front part and a back part. The coronal plane may refer to a plane that is vertical to the ground and divides the target object into a right part and a left part. In some embodiments, the method of the image recombination may include but is not limited to multi-planar reconstruction (MPR). The 3D reconstruction may obtain a 3D image of a liver based on a 2D image of the liver (e.g., a CT scan image of a cross section of the liver, a CT scan image of a coronal plane of the liver, a CT scan image of a sagittal plane of the liver, etc.). The image filtering may be used to suppress the noise of an image under a condition of keeping the details of the image as many as possible. The image filtering may include, but is not limited, Gaussian filtering, linear filtering (e.g., median filtering), nonlinear filtering, limited amplitude wave filtering, algorithmic average filtering, recursive average filtering, first order lag filtering, high-pass filtering, low-pass filtering, K nearest neighbor filtering (KNN), or the like, or any combination thereof. The image format conversion may represent the format conversion of an image. For example, the image acquisition unit 410 may convert a CT image from a digital imaging and communication in medicine (DCM) format into a visualization toolkit grid format (VTI). The image coding may be referred to as image compression, and may indicate that an image or information included in the image is represented by fewer bits in a condition that the image quality (e.g., signal-to-noise ratio) is high enough. The image rendering may transform high dimensional information into low dimensional information. For example, the image rendering may transform 3D information into 2D information.

In some embodiments, the image acquisition module 410 may obtain scan data from the imaging device 110 and generate an original image based on the scan data. For example, for a CT scan image, the imaging device 110 may scan a section of a certain thickness of a subject using an X-ray beam. The imaging device 110 may receive X-rays that are passed through the section. The X-rays may be converted into visible light. Optical signals of the visible light may be converted into electric signals. The electric signals may be converted into digital signals by an analog digital converter. The image acquisition module 410 in the processing device 130 may obtain the digital signals. The scanned section may be divided into a plurality of cuboids having an equal volume during a process of processing the digital signals. The image acquisition module 410 may determine an X-ray attenuation coefficient of each cuboid based on the digital signals, and arrange the X-ray attenuation coefficient of each cuboid in a digital matrix. A digital analog converter may convert the digital matrix into a plurality of rectangles (e.g., pixels) having an equal area and different gray values. The image acquisition module 410 may arrange the plurality of rectangles based on the digital matrix to obtain a 2D CT scan image.

In some embodiments, the image acquisition module 410 may obtain a processed image by processing an original image. In some embodiments, the image acquisition module 410 may obtain an original image and/or a processed image from a storage apparatus (e.g., the database 140). In some embodiments, the original image obtained by reconstructing the scan data and/or the processed image obtained by processing the original image may be stored in a storage apparatus (e.g., the database 140, a storage device in the processing device 130), or may be sent to other modules for further processing (e.g. sent to the ROI determination module 430 to determine an ROI or sent to the segmentation information acquisition module 440 to obtain segmentation information).

In 520, the segmentation protocol acquisition module 420 may obtain a segmentation protocol. In some embodiments, the segmentation protocol may be used to determine how to segment a liver in the scan image. In some embodiments, the segmentation protocol may include, but is not limited to, segmentation relating to a hepatic left lobe and a hepatic right lobe, segmentation relating to hepatic left three lobes, segmentation relating to hepatic right three lobes, segmentation relating to a hepatic middle lobe, segmentation relating to an upper segment and a lower segment of the hepatic right lobe, segmentation relating to hepatic four lobes, segmentation relating to hepatic five segments, segmentation relating to hepatic six segments, segmentation relating to hepatic seven segments, segmentation relating to hepatic eight segments, or the like, or any combination thereof.

In some embodiments, the segmentation protocol may be automatically obtained by the segmentation protocol acquisition module 420 from a storage apparatus (e.g., the database 140 or a storage device of the processing device 130), or may be input by a user (e.g., a doctor or an imaging technician) through an I/O device in the processing device 130, or may be obtained by the segmentation protocol acquisition module 420 from any external resource via the network 120.

In 530, the ROI determination module 430 may determine an ROI based on the scan image. The ROI may include but is not limited to a target object. In some embodiments, the ROI determination module 430 may obtain the ROI automatically. In some embodiments, a user (e.g., a doctor or an imaging technician) may determine the ROI manually. Instructions relating to determining the ROI may be sent to the ROI determination module 430 through the I/O device in the processing device 130. The ROI determination module 430 may determine the ROI based on the received instructions.

In 540, the segmentation acquisition module 440 may obtain segmentation information based on the ROI. The segmentation information may include, but is not limited to, image information and/or ROI information. The image information may include but not limited to image grayscale information and/or image structure information. The image grayscale information may include, but is not limited to, image data matrix, image spectrum, image 2D histogram, or the like, or any combination thereof. In some embodiments, the image spectrum may be obtained based on image transformation. The image transformation may include, but is not limited to, Fourier transformation, sine transformation (e.g., discrete cosine transformation), cosine transformation, Gabor transformation, wavelet transformation, or the like, or any combination thereof. The image structure information may include, but is not limited to, image corner information, image gradient information, image structure tensor information, image curvature, or the like, or any combination thereof.

In some embodiments, the ROI information may include, but is not limited to, structure information of a target object and/or blood vessel information of a target object. In some embodiments, the structure information may include structure information of a liver. The structure information of a liver may refer to information related to liver composition and liver surface morphology. For example, the structure information of a liver may include, but is not limited to, location information of the hepatic duct 310, the ligamentum teres hepatis 311, falciform ligament (not shown in the drawings), grooves of hepatic surface (e.g., a hepatic left longitudinal groove), fossae of hepatic surface (e.g., a gallbladder fossa), fissures of hepatic surface (e.g., a middle hepatic fissure), or the like, or any combination thereof. The blood vessel information of a target object may include blood vessel information of a liver. The blood vessel information of a liver may refer to information related to the distribution of blood vessels in the liver. For example, blood vessel information of a liver may include, but is not limited to, vascular contour information and/or vascular location information. The vascular contour information may include, but is not limited to, locations of the right hepatic vein 301, the middle hepatic vein 302, the left hepatic vein 303, the inferior vena cava 304, the hepatic portal vein 305, or the hepatic artery 309 in the liver, vascular intersections (e.g., an intersection of the right hepatic vein 301, the middle hepatic vein 302, the left hepatic vein 303, and the inferior vena cava 304), morphological information of blood vessels (e.g., the hepatic portal vein 305 may include the left branch 312 and the right branch 313, locations of forks on the hepatic portal vein 305, locations of forks on the left branch 312 of the hepatic portal vein 305 and/or the right branch 313 of hepatic portal vein 305). In some embodiments, the method of obtaining the blood vessel information of a target object may include, but is not limited to, a threshold-based segmentation algorithm, a region-based segmentation algorithm, an edge-based segmentation algorithm, a segmentation algorithm based on a specific theory, etc.

In 550, the segmentation module 450 may generate a segmentation result by segmenting the ROI based on the segmentation information and the segmentation protocol. In some embodiments, the segmentation module 450 may segment a liver in the scan image based on the structure information of the liver and/or the blood vessel information of the liver. For example, the segmentation module 450 may segment a liver into a hepatic left lobe and a hepatic right lobe based on the position of the falciform ligament in the liver. As another example, the segmentation module 450 may segment a liver based on the distribution of blood vessels in the liver. As still another example, the segmentation module 450 may segment a liver based on the distribution of blood vessels and the surface morphology (e.g., the position of the gallbladder fossa and the liver fissure in the liver) of the liver.

In some embodiments, the segmentation result may be presented in a visual manner. For example, the segmentation result may be displayed on the scan image (as shown in FIGS. 10-A to 10-D).

In some embodiments, the segmentation result may be used in a liver surgery. For example, after the segmentation result of a liver in the scan image is generated, the processing device 130 may determine a surgical plan for a liver surgery based on the segmentation result. The surgical plan may include determining a necessary resection region of a liver to remove a target lesion thoroughly, determining a necessary remaining region of the liver, determining an appropriate resection region of the liver, determining a surgical procedure, determining a surgical technique, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in some embodiments, 510 may be performed before or after 520, or 510 and 520 may be performed simultaneously. As another example, in some embodiments, 530 of determining the ROI may be an optional step. As still another example, in some embodiments, after 550, an operation to display the segmentation result may be added.

Figure 6:
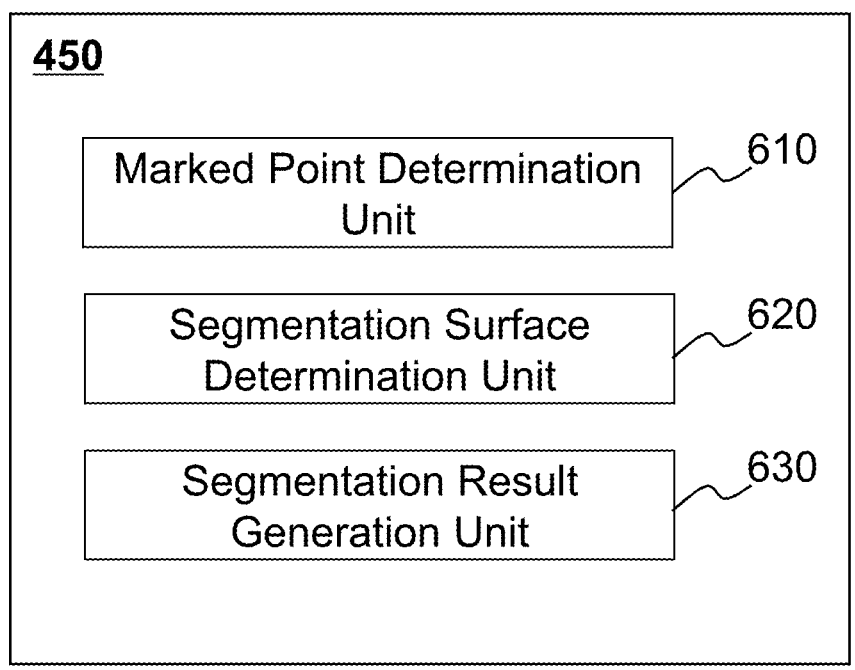
FIG. 6 is a block diagram illustrating an exemplary segmentation module according to some embodiments of the present disclosure.

FIG. 6 is a block diagram illustrating an exemplary segmentation module according to some embodiments of the present disclosure. The segmentation module 450 may include a marked point determination unit 610, a segmentation surface determination unit 620, and a segmentation result generation unit 630. The modules described in FIG. 6 may be implemented by the CPU 270 of the computing device 200 as shown in FIG. 2. The modules may be directly (and/or indirectly) connected to each other. It should be noted that the segmentation module 450 described in FIG. 6 is merely provided for purpose of illustration, and not intended limit the scope of the application in said embodiments. It is understood for persons having ordinary skills in the art, multiple variations and modifications of the description of the segmentation module 450 in application field and details may be made under the teachings of the present disclosure based on the mechanism. For example, two of the modules may be combined as a single module, or one of the modules may be divided into two or more modules.

The marked point determination unit 610 may determine one or more marked points. The one or more marked points may be used to label a liver in the scan image to determine one or more segmentation surfaces of the liver. A marked point may be represented as a pixel or a voxel in the scan image. The pixel may refer to the smallest unit included in a 2D image, and the voxel may refer to the smallest unit included in a 3D image. In some embodiments, the one or more marked points may include a feature point of blood vessels of the liver and/or a feature point of surface morphology of the liver. The feature point of the blood vessels of the liver may include, but are not limited to, a point on a hepatic portal (P point), a venous intersection point (V point), a point on a middle hepatic vein (MV point), a point on a right hepatic vein (RV point), a fork on a left branch of a portal vein (LP point), a fork on a right branch of a portal vein (RP point), or the like, or any combination thereof. The feature point of the surface morphology of the liver may include, but is not limited to, a hepatic fissure point (LF point) and a small hepatic fissure point of a hepatic left lobe. The point on the hepatic portal may be located at a fork of the hepatic portal vein 305. The venous intersection point may be located at the intersection of the right hepatic vein 301, the left hepatic vein 303, the middle hepatic vein 302, and the inferior vena cava 304. The point on the middle hepatic vein may be located on the middle hepatic vein 302. The point on the right hepatic vein may be located on the right hepatic vein 301. The fork on the left branch of the portal vein may be located at the first fork, along the direction from the outside to the inside of the liver, on the left branch 312 of the hepatic portal vein 305. The fork on the right branch of the portal vein may be located at the first fork, along the direction from the outside to the inside of the liver, on the right branch 313 of the hepatic portal vein 305. The hepatic fissure point (LF point) may be located on the ligamentum teres hepatis 311.

In some embodiments, the marked point may be determined in an automatic way and/or a manual way (e.g., the marked point may be determined manually by a doctor or an imaging technician). For example, the marked point determination unit 610 may automatically determine the one or more marked points based on the segmentation information. As another example, a user (e.g., a doctor or an imaging technician) may manually determine the one or more marked points, and send an instruction relating to determining the one or more marked points to the marked point determination unit 610 through the I/O device in the processing device 130. The marked point determination unit 610 may obtain the instruction and determine the one or more marked points based on the instruction. As still another example, the marked point determination unit 610 may first determine the one or more marked points automatically based on the segmentation information. Then, the user (e.g., a doctor and an imaging technician) may manually adjust (e.g., add one or more new marked points, delete at least one of the one or more marked points, change the location of at least one of the one or more marked points, etc.) the one or more marked points determined by the marked point determination unit 610 automatically. Instructions relating to adjusting the one or more marked points may be sent to the marked point determination unit 610 through the I/O device in the processing device 130. The marked point determination unit 610 may update the one or more marked points based on the received instructions relating to adjusting the one or more marked points.

The segmentation surface determination unit 620 may determine one or more segmentation surfaces. A segmentation surface may be used to segment a liver in the scan image. The segmentation surface may be a segmentation flat surface or a segmentation curved surface. In some embodiments, the one or more segmentation surfaces may be determined in an automatic way and/or a manual way (e.g., the one or more segmentation surfaces may be determined manually by a doctor or an imaging technician). For example, the segmentation surface determination unit 620 may automatically determine the one or more segmentation surfaces based on the one or more marked points. As another example, a user (e.g., a doctor or an imaging technician) may manually determine the one or more segmentation surfaces, and send an instruction relating to determining the one or more segmentation surfaces to the segmentation surface determination unit 620 through the I/O device in the processing device 130. The segmentation surface determination unit 620 may obtain the instruction and determine the one or more segmentation surfaces based on the instruction. As still another example, the segmentation surface determination unit 620 may first determine one or more segmentation surfaces automatically based on the one or more marked points. Then, the user (e.g., a doctor and an imaging technician) may manually adjust (e.g., add one or more new segmentation surfaces, delete at least one of the one or more segmentation surfaces, change the angle, the location, or the size of at least one of the one or more segmentation surfaces, etc.) the one or more segmentation surfaces determined by the segmentation surface determination unit 620 automatically. Instructions relating to adjusting the one or more segmentation surfaces may be sent to the segmentation surface determination unit 620 through the I/O device in the processing device 130. The segmentation surface determination unit 620 may update the one or more segmentation surfaces based on the received instructions relating to adjusting the one or more segmentation surfaces.

The segmentation result generation unit 630 may generate a segmentation result of the target object. In some embodiments, the segmentation result may correspond to a segmentation protocol. For example, if the segmentation protocol is the segmentation relating to the hepatic left lobe and the hepatic right lobe, the segmentation result may indicate that a liver in the scan image is segmented into a left lobe and a right lobe by the segmentation surface determined by the segmentation surface determination unit 620. As another example, if the segmentation protocol is the segmentation relating to the hepatic four lobes, the segmentation result may indicate that a liver in the scan image is segmented into a right anterior lobe, a right posterior lobe, a left medial lobe (liver segment 4), and a left lateral lobe by the segmentation surfaces determined by the segmentation surface determination unit 620. In some embodiments, the segmentation result may be presented in a visual manner. For example, the segmentation result may be displayed on the scan image (as shown in FIGS. 10-A to 10-D).

Figure 7:
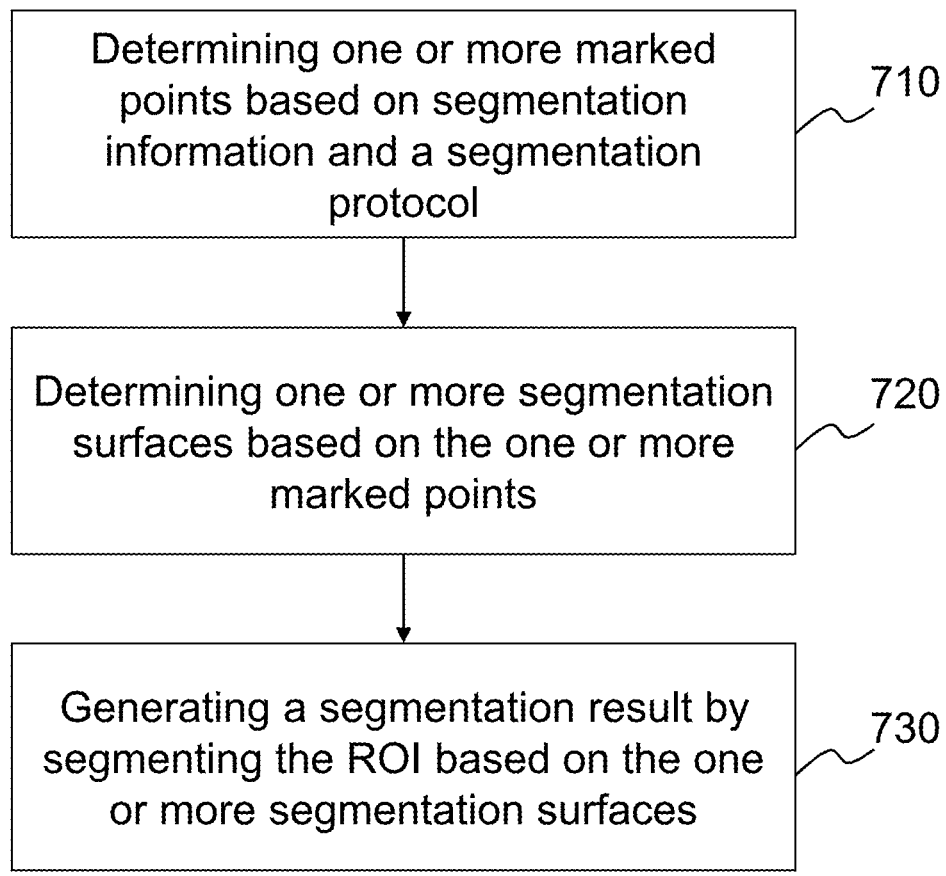
FIG. 7 is a flowchart illustrating an exemplary process for segmenting a region of interest (ROI) according to some embodiments of the present disclosure.

FIG. 7 is a flowchart illustrating an exemplary process for segmenting a region of interest (ROI) according to some embodiments of the present disclosure. In some embodiments, step 550 of the process 500 in FIG. 5 may be performed based on the process 700.

In 710, the marked point determination unit 610 may determine one or more marked points based on segmentation information and a segmentation protocol.

In some embodiments, for the segmentation relating to the hepatic left lobe and the hepatic right lobe, the marked point determination unit 610 may determine one or more P points, one or more V points, and one or more MV points. For the segmentation relating to the hepatic left three lobes, the marked point determination unit 610 may determine one or more P points, one or more V points, one or more RV points, or one or more MV points. For the segmentation relating to the hepatic right three lobes, the marked point determination unit 610 may determine one or more P points, one or more V points, one or more LF points, one or more LP points, or one or more MV points. For the segmentation relating to the hepatic middle lobe, the marked point determination unit 610 may determine one or more P points, one or more V points, one or more RV points, one or more LF points, one or more LP points, or one or more MV points. For the segmentation relating to the upper segment and the lower segment of the hepatic right lobe, the marked point determination unit 610 may determine one or more P points, one or more V points, one or more RP points, and one or more MV points. For the segmentation relating to the hepatic four lobes, the marked point determination unit 610 may determine one or more P points, one or more V points, one or more RV points, one or more LF points, one or more LP points, and one or more MV points. For the segmentation relating to the hepatic five segments, the marked point determination unit 610 may determine one or more P points, one or more V points, one or more RV points, one or more LF points, one or more LP points, and one or more MV points. For the segmentation of hepatic six segments, the marked point determination unit 610 may determine one or more P points, one or more V points, one or more RP points, one or more RV points, one or more LP points, one or more LF points, and one or more MV points. For the segmentation of hepatic seven segments, the marked point determination unit 610 may determine one or more P points, one or more V points, one or more RP points, one or more RV points, one or more LF points, one or more LP points, and one or more MV points. For the segmentation of hepatic eight segments, the marked point determination unit 610 may determine one or more P points, one or more V points, one or more RP points, one or more RV points, one or more LF points, one or more LP points, one or more MV points, and a small hepatic fissure point of the hepatic left lobe.

In some embodiments, the marked point determination unit 610 may determine the one or more marked points based on structure information of a liver. For example, the marked point determination unit 610 may determine a point located at the ligamentum teres hepatis of the liver in the scan image as a marked points (e.g., a hepatic fissure point). As another example, the marked point determination unit 610 may determine a point located at the gallbladder fossa of the liver in the scan image as a marked point. As still another example, the marked point determination unit 610 may determine a point located at the left longitudinal groove of the liver in the scan image as a marked point.

In some embodiments, the marked point determination unit 610 may determine the one or more marked points based on the blood vessel information of the liver. For example, the marked point determination unit 610 may determine a point (e.g., the point on the middle hepatic vein) located on the middle hepatic vein 302 of the liver in the scan image as a marked point. As another example, the marked point determination unit 610 may determine a point (e.g., the venous intersection point) located at the intersection of the right hepatic vein 301, the middle hepatic vein 302, the left hepatic vein 303, and the inferior vena cava 304 of the liver in the scan image as a marked point. As still another example, the marked point determination unit 610 may determine a point (e.g., the fork on the right branch of the hepatic portal point) located at the first fork, along the direction from the outside to the inside of the liver, of the right branch 312 of the hepatic portal vein 305 of the liver in the scan image as a marked point.

In some embodiments, the one or more marked points may be determined based on an algorithm based on vascular centerline, a vessel tracking algorithm, an algorithm based on vascular structure analysis, or the like, or any combination thereof.

In 720, the segmentation surface determination unit 620 may determine one or more segmentation surfaces based on the one or more marked points. In some embodiments, a segmentation surface may be a segmentation flat surface or a segmentation curved surface. In some embodiments, the segmentation surface determination unit 620 may determine the segmentation flat surface based on the one or more marked points. The segmentation flat surface may be used to segment the liver in the scan image and/or determine the segmentation curved surface. In some embodiments, the segmentation surface determination unit 620 may determine a segmentation flat surface based on three or more marked points. For example, the segmentation surface determination unit 620 may determine a segmentation flat surface based on a P point, a V point and an MV point. The determined segmentation flat surface may be used to segment the liver in the scan image into a left lobe and a right lobe, and/or determine a segmentation curved surface that is used to segment the liver in the scan image into a left lobe and a right lobe. The segmentation surface determination unit 620 may determine a segmentation flat surface based on a P point, a V point, an LF point, and an LP point. The segmentation flat surface may be used to segment a left lobe of the liver in the scan image into a left medial lobe (liver segment 4) and a left lateral lobe, and/or determine a segmentation curved surface that is used to segment the left lobe into a left medial lobe (liver segment 4) and a left lateral lobe. The segmentation surface determination unit 620 may determine a segmentation flat surface based on a P point, a V point, and an RV point. The segmentation flat may be used to segment a right lobe of the liver in the scan image into a right anterior lobe and a right posterior lobe, and/or determine a segmentation curved surface that is used to segment the right lobe into a right anterior lobe and a right posterior lobe.

In some embodiments, the segmentation surface determination unit 620 may determine a segmentation flat surface based on a marked point and a cross section. For example, the segmentation surface determination unit 620 may determine a segmentation flat surface based on an LP point and a cross section. The segmentation flat surface may be used to segment a left lateral lobe of the liver in the scan image into an upper segment (liver segment 2) and a lower segment (liver segment 3). The segmentation flat surface may be parallel to the cross section and pass through the LP point. As another example, the segmentation surface determination unit 620 may determine a segmentation flat surface based on an RP point and a cross section. The segmentation flat surface may segment a right lobe of the liver in the scan image into an upper segment and a lower segment. The segmentation flat surface may be parallel to the cross section and pass through the RP point. The cross section may refer to a plane that is parallel to the ground and divides the target object into an upper part and a lower part. The sagittal plane may refer to a plane that is vertical to the ground and divides the target object into a front part and a back part. The coronal plane may refer to a plane that is vertical to the ground and divides the target object into a right part and a left part.

In some embodiments, the segmentation result generated by segmenting the liver in the scan image using the segmentation flat surface(s) may be incorrect. Therefore, the liver in the scan image may be segmented by one or more segmentation curved surfaces. The segmentation surface determination unit 620 may determine a plurality of segmentation flat surfaces based on the one or more marked points, and then determine a segmentation curved surface based on the plurality of segmentation flat surfaces. For example, the marked point determination unit 610 may determine a P point, a V point, and three MV points (e.g., $MV_1$, $MV_2$, $MV_3$). The segmentation surface determination unit 620 may determine a segmentation flat surface $P_1$ based on the P point, the V point, and the $MV_1$ point, a segmentation flat surface $P_2$ based on the P point, the V point, and the $MV_2$ point, and a segmentation flat surface $P_3$ based on the P point, the V point, and the $MV_3$ point. The segmentation surface determination unit 620 may determine a segmentation curved surface based on the segmentation flat surface $P_1$, the segmentation flat surface $P_2$, and the segmentation flat surface $P_3$ to segment the liver in the scan image into a left lobe and a right lobe.

In 730, the segmentation result generation unit 630 may generate a segmentation result by segmenting the ROI in the scan image based on the one or more segmentation surfaces. In some embodiments, the segmentation result generation unit 630 may segment the ROI based on a segmentation flat surface and/or a segmentation curved surface. In some embodiments, the segmentation result may correspond to a segmentation protocol. For example, if the segmentation protocol is the segmentation relating to the hepatic left lobe and the hepatic right lobe, the segmentation result may indicate that the liver in the scan image is segmented into a left lobe and a right lobe by the segmentation surface determined by the segmentation surface determination unit 620. As another example, if the segmentation protocol is the segmentation relating to the hepatic four lobes, the segmentation result may indicate that the liver in the scan image is segmented into a right anterior lobe, a right posterior lobe, a left medial lobe (liver segment 4), and a left lateral lobe by the segmentation surfaces determined by the segmentation surface determination unit 620. In some embodiments, the segmentation result may be presented in a visual manner. For example, the segmentation result may be displayed on the scan image (as shown in FIGS. 10-A to 10-D).

In some embodiments, different marked points or different combinations of the marked points may be used to determine different segmentation surfaces. For example, a P point, a V point, and an MV point may be used to determine a segmentation surface that segments the liver in the scan image into a left lobe and a right lobe. A P point, a V point, and an RV point may be used to determine a segmentation surface that segments a right lobe of the liver in the scan image into a right anterior lobe and a right posterior lobe. A P point, a V point, an LF point, and an LP point may be used to determine a segmentation surface that segments a left lobe of the liver in the scan image into a left medial lobe and a left lateral lobe (liver segment 4). An RP point may be used to determine a segmentation surface that segments a right lobe of the liver in the scan image into an upper segment lobe and a lower segment. An LP point may be used to determine a segmentation surface that segments a left lateral lobe into an upper segment (liver segment 2) and a lower segment (liver segment 3). Therefore, different segmentation surfaces may be determined based on different marked points and/or different combinations of the marked points to achieve different segmentation protocols.

For example, for the segmentation relating to the hepatic left lobe and the hepatic right lobe, the marked point determination unit 610 may determine one or more P points, one or more V points, and one or more MV points. The segmentation surface determination unit 620 may determine a segmentation surface that segments the liver in the scan image into a left lobe and a right lobe based on the one or more P points, the one or more V points, and the one or more MV points. The segmentation result generation unit 630 may generate a segmentation result based on the determined segmentation surface. The segmentation result may indicate that the liver in the scan image is segmented into a left lobe and a right lobe by the determined segmentation surface.

For the segmentation relating to the hepatic left three lobes, the marked point determination unit 610 may determine one or more P points, one or more V points, one or more MV points, and one or more RV points. The segmentation surface determination unit 620 may determine a segmentation surface that segments the liver in the scan image into a left lobe and a right lobe based on the one or more P points, the one or more V points, and the one or more MV points. The segmentation surface determination unit 620 may also determine a segmentation surface that segments the right lobe into a right anterior lobe and a right posterior lobe based on the one or more P points, the one or more V points, and the one or more RV points. The segmentation result generation unit 630 may combine the left lobe and the right anterior lobe as the left three lobes. The segmentation result generation unit 630 may generate a segmentation result indicating that the liver in the scan image is segmented into a right anterior lobe and left three lobes by the determined segmentation surfaces.

Alternatively, the marked point determination unit 610 may determine one or more P points, one or more V points, and one or more RV points. The segmentation surface determination unit 620 may determine a segmentation surface that segments the right lobe into a right anterior lobe and a right posterior lobe based on the one or more P points, the one or more V points, and the one or more RV points. The segmentation result generation unit 630 may generate a segmentation result indicating that the liver in the scan image is segmented into a right anterior lobe and left three lobes by the determined segmentation surface. This operation omits the process of determining the segmentation surface that segments the liver in the scan image into a left lobe and a right lobe.

For the segmentation relating to the hepatic right three lobes, the marked point determination unit 610 may determine one or more P points, one or more V points, one or more MV points, one or more LP points, and one or more LF points. The segmentation surface determination unit 620 may determine a segmentation surface that segments the liver in the scan image into a left lobe and a right lobe based on the one or more P points, the one or more V points, and the one or more MV points. The segmentation surface determination unit 620 may also determine a segmentation surface that segments the left lobe into a left medial lobe (liver segment 4) and a left lateral lobe based on the one or more P points, the one or more V points, the one or more LP points, and the one or more LF points. The segmentation result generation unit 630 may combine the left medial lobe (liver segment 4) and the right lobe as the right three lobes. The segmentation result generation unit 630 may generate a segmentation result indicating that the liver in the scan image is segmented into a left lateral lobe and right three lobes by the determined segmentation surfaces.

Alternatively, the marked point determination unit 610 may determine one or more P points, one or more V points, one or more LP points, and one or more LF points. The segmentation surface determination unit 620 may determine a segmentation surface that segments the left lobe into a left medial lobe (liver segment 4) and a left lateral lobe based on the one or more P points, the one or more V points, the one or more LP points, and the one or more LF points. The segmentation result generation unit 630 may generate a segmentation result indicating that the liver in the scan image is segmented into a left lateral lobe and right three lobes by the determined segmentation surface. This operation omits the process of determining the segmentation surface that segments the liver in the scan image into a left lobe and a right lobe.

For the segmentation relating to the hepatic middle lobe, the marked point determination unit 610 may determine one or more P points, one or more V points, one or more MV points, one or more RV points, one or more LP points, and one or more LF points. The segmentation surface determination unit 620 may determine a segmentation surface that segments the liver in the scan image into a left lobe and a right lobe based on the one or more P points, the one or more V points, and the one or more MV points. The segmentation surface determination unit 620 may also determine a segmentation surface that segments the right lobe into a right anterior lobe and a right posterior lobe based on the one or more P points, the one or more V points, and the one or more RV points. The segmentation surface determination unit 620 may also determine a segmentation surface that segments the left lobe into a left lateral lobe and a left medial lobe (liver segment 4) based on the one or more P points, the one or more V points, the one or more LP points, and the one or more LF points. The segmentation result generation unit 630 may combine the left medial lobe (liver segment 4) and the right anterior lobe as the hepatic middle lobe. The segmentation result generation unit 630 may generate a segmentation result indicating that the liver in the scan image is segmented into a right posterior lobe, a hepatic middle lobe, and a left lateral lobe by the determined segmentation surfaces.

Alternatively, the marked point determination unit 610 may determine one or more P points, one or more V points, one or more RV points, one or more LP points, and one or more LF points. The segmentation surface determination unit 620 may determine a segmentation surface that segments the right lobe into a right anterior lobe and a right posterior lobe based on the one or more P points, the one or more V points, and the one or more RV points. The segmentation surface determination unit 620 may also determine a segmentation surface that segments the left lobe into a left medial lobe (liver segment 4) and a left lateral lobe based on the one or more P points, the one or more V points, the one or more LP points, and the one or more LF points. The segmentation result generation unit 630 may generate a segmentation result indicating that the liver in the scan image is segmented into a right posterior lobe, a middle lobe, and a left lateral lobe by the determined segmentation surfaces. This operation omits the process of determining the segmentation surface that segments the liver in the scan image into a left lobe and a right lobe.

For the segmentation relating to the upper segment and the lower segment of the hepatic right lobe, the marked point determination unit 610 may determine one or more P points, one or more V points, one or more MV points, and one or more RP points. The segmentation surface determination unit 620 may determine a segmentation surface that segments the liver in the scan image into a right lobe and a left lobe based on the one or more P points, the one or more V points, and the one or more MV points. The segmentation surface determination unit 620 may also determine a segmentation surface that segments the right lobe into an upper segment and a lower segment based on the one or more RP points. The segmentation result generation unit 630 may generate a segmentation result indicating that the liver in the scan image is segmented into a left lobe, an upper segment of a right lobe, and a lower segment of the right interior lobe by the determined segmentation surfaces.

For the segmentation relating to the hepatic four lobes, the marked point determination unit 610 may determine one or more P points, one or more V points, one or more MV points, one or more RV points, one or more LP points, and one or more LF points. The segmentation surface determination unit 620 may determine a segmentation surface that segments the liver in the scan image into a right lobe and a left lobe based on the one or more P points, the one or more V points, and the one or more MV points. The segmentation surface determination unit 620 may also determine a segmentation surface that segments the right lobe into a right anterior lobe and a right posterior lobe based on the one or more P points, the one or more V points, and the one or more RV points. The segmentation surface determination unit 620 may also a segmentation surface that segments the left lobe into a left medial lobe (liver segment 4) and a left lateral lobe based on the one or more P points, the one or more V points, the one or more LP points, and the one or more LF points. The segmentation result generation unit 630 may generate a segmentation result indicating that the liver in the scan image is segmented into a right anterior lobe, a right posterior lobe, a left medial lobe, and a left lateral lobe (liver segment 4) by the determined segmentation surfaces.

For the segmentation of the hepatic five segments, the marked point determination unit 610 may determine one or more P points, one or more V points, one or more MV points, one or more RV points, one or more LP points, and one or more LF points. The segmentation surface determination unit 620 may determine a segmentation surface that segments the liver in the scan image into a right lobe and a left lobe based on the one or more P points, the one or more V points, and the one or more MV points. The segmentation surface determination unit 620 may also determine a segmentation surface that segments the right lobe into a right anterior lobe and a right posterior lobe based on the one or more P points, the one or more V points, and the one or more RV points. The segmentation surface determination unit 620 may also determine a segmentation surface that segments the left lobe into a left medial lobe (liver segment 4) and a left lateral lobe based on the one or more P points, the one or more V points, the one or more LP points, and the one or more LF points. The segmentation surface determination unit 620 may also determine a segmentation surface that segments the left lateral lobe into an upper segment (liver segment 2) and a lower segment (liver segment 3) based on the one or more LP points and a cross section. The segmentation result generation unit 630 may generate a segmentation result indicating that the liver in the scan image is segmented into a right anterior lobe, a right posterior lobe, a left medial lobe (liver segment 4), an upper segment of the left lateral lobe (liver segment 2), and a lower segment of the left lateral lobe (liver segment 3) by the determined segmentation surfaces.

For the segmentation relating to the hepatic six segments, the marked point determination unit 610 may determine one or more P points, one or more V points, one or more MV points, one or more RV points, one or more RP points, one or more LP points, and one or more LF points. The segmentation surface determination unit 620 may determine a segmentation surface that segments the liver in the scan image into a right lobe and a left lobe based on the one or more P points, the one or more V points, and one or more MV points. The segmentation surface determination unit 620 may also determine a segmentation surface that segments the right lobe into a right anterior lobe and a right posterior lobe based on the one or more P points, the one or more V points, and the one or more RV points. The segmentation surface determination unit 620 may also determine a segmentation surface that segments the left lobe into a left medial lobe (liver segment 4) and a left lateral lobe based on the one or more P points, the one or more V points, the one or more LP points, and the one or more LF points. The segmentation surface determination unit 620 may also determine a segmentation surface that segments the right lobe into an upper segment and a lower segment based on the one or more RP points and a cross section. The segmentation result generation unit 630 may generate a segmentation result indicating that the liver in the scan image is segmented into an upper segment of a right anterior lobe (liver segment 8), a lower segment of the right anterior lobe (liver segment 5), an upper segment of a right posterior lobe (liver segment 7), a lower segment of the right posterior lobe (liver segment 6), a left medial lobe (liver segment 4), and a left lateral lobe by the determined segmentation surfaces.

For the segmentation of the hepatic seven segments, the marked point determination unit 610 may determine one or more P points, one or more V points, one or more MV points, one or more RV points, one or more RP points, one or more LP points, and one or more LF points. The segmentation surface determination unit 620 may determine a segmentation surface that segments the liver in the scan image into a right lobe and a left lobe based on the one or more P points, the one or more V points, and the one or more MV points. The segmentation surface determination unit 620 may also determine a segmentation surface that segments the right lobe into a right anterior lobe and a right posterior lobe based on the one or more P points, the one or more V points, and the one or more RV points. The segmentation surface determination unit 620 may also determine a segmentation surface that segments the left lobe into a left medial lobe (liver segment 4) and a left lateral lobe based on the one or more P points, the one or more V points, the one or more LP points, and the one or more LF points. The segmentation surface determination unit 620 may also determine a segmentation surface that segments the left lobe into an upper segment (liver segment 2) and a lower segment (liver segment 3) based on the one or more LP points and a cross section. The segmentation surface determination unit 620 may also determine a segmentation surface that segments the right lobe into an upper segment and a lower segment based on the one or more RP points and a cross section. The segmentation result generation unit 630 may generate a segmentation result indicating that the liver in the scan image is segmented into an upper segment of a right anterior lobe (liver segment 8), a lower segment of the right anterior lobe (liver segment 5), an upper segment of a right posterior lobe (liver segment 7), a lower segment of the right posterior lobe (liver segment 6), a left medial lobe (liver segment 4), an upper segment of a left lateral lobe (liver segment 2), and a lower segment of the left lateral lobe (liver segment 3) by the determined segmentation surfaces.

For the segmentation of the hepatic eight segments, after determining the hepatic seven segments, the segmentation module 450 may determine the caudate lobe (liver segment 1) based on the locations of the inferior vena cava 304 and the hepatic portal vein 305. Alternatively, the segmentation module 450 may automatically determine the caudate lobe (liver segment 1) by automatically determining the small hepatic fissure point of the hepatic left lobe.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in some embodiments, after 730, an operation of displaying or storing the segmentation result may be added.

Figure 8:
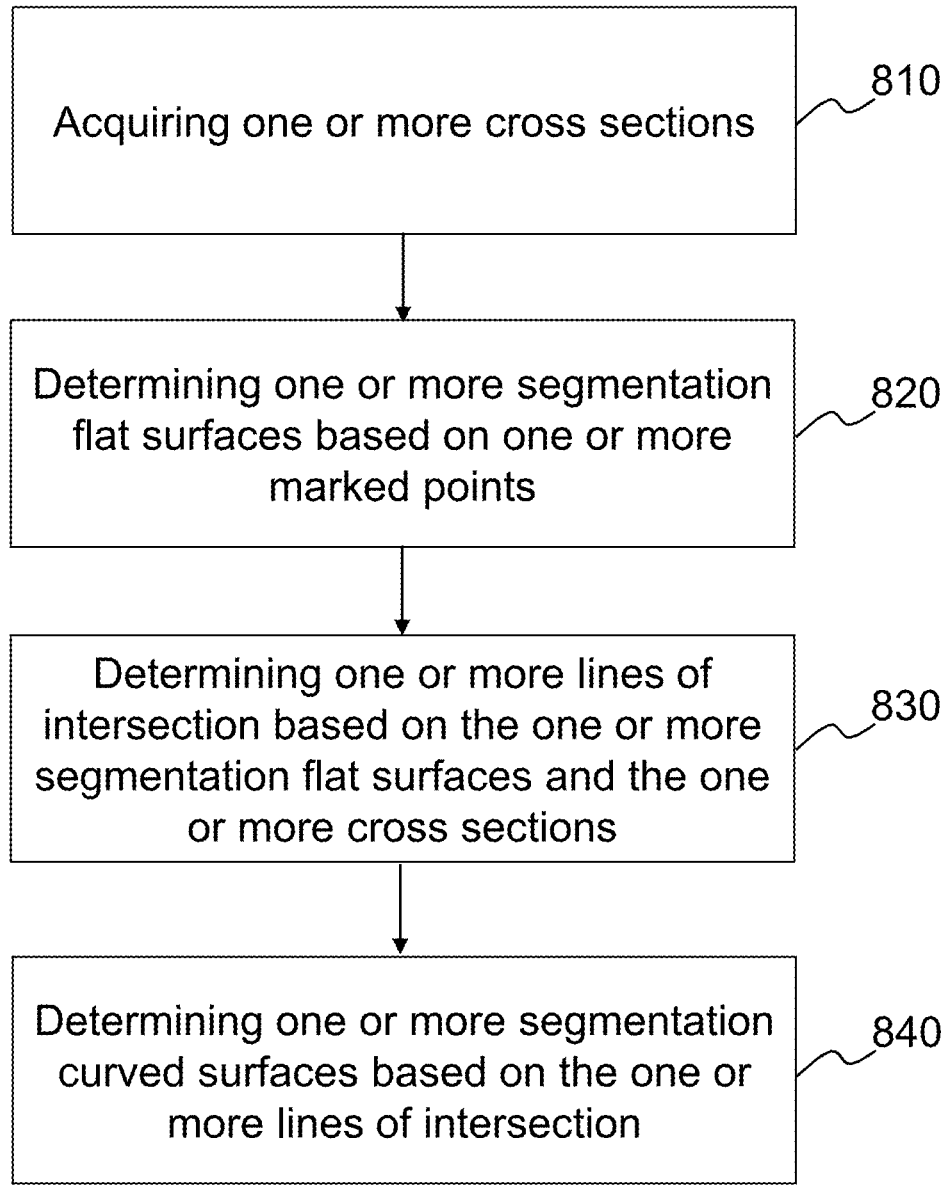
FIG. 8 is a flowchart illustrating an exemplary process for determining one or more segmentation curved surfaces according to some embodiments of the present disclosure.

FIG. 8 is a flowchart illustrating an exemplary process for determining one or more segmentation curved surfaces according to some embodiments of the present disclosure. In some embodiments, step 720 of the process 700 in FIG. 7 may be performed based on the process 800. In some embodiments, if the liver in the scan image is segmented by one or more segmentation flat surfaces, the segmentation result may be incorrect. Therefore, it is desirable to segment the liver in the scan image using one or more continuous and smooth segmentation curved surfaces.

In 810, the segmentation surface determination unit 620 may obtain one or more cross sections. The cross section may refer to a plane that is parallel to the ground and divides the target object into an upper part and a lower part.

In 820, the segmentation surface determination unit 620 may determine one or more segmentation flat surfaces based on one or more marked points and the cross section. In some embodiments, the segmentation surface determination unit 620 may determine a segmentation flat surface based on three or more marked points. For example, the segmentation surface determination unit 620 may determine a segmentation flat surface that segments the liver in the scan image into a left lobe and a right lobe based on a P point, a V point, and an MV point. As another example, the segmentation surface determination unit 620 may determine a segmentation flat surface that segments a left lobe of the liver in the scan image into a left lateral lobe and a left medial lobe (liver segment 4) based on a P point, a V point, an LF point, and an LP point. In some embodiments, a segmentation flat surface may be determined by determining a plane equation based on 3D coordinates of the three or more marked points. The plane equation may be a linear equation in three unknowns. The plane equation may include, but is not limited to, an intercept form equation, a point normal form equation, a normal form equation, a general form equation, or the like, or any combination thereof.

In some embodiments, the segmentation surface determination unit 620 may determine a segmentation flat surface based on a marked point and a cross section. For example, the segmentation surface determination unit 620 may determine a segmentation flat surface based on an LP point and a cross section. The segmentation flat surface may be used to segment a left lateral lobe of the liver in the scan image into an upper segment (liver segment 2) and a lower segment (liver segment 3). The segmentation flat surface may be parallel to the cross section and pass through the LP point. As another example, the segmentation surface determination unit 620 may determine a segmentation flat surface based on an RP point and a cross section. The segmentation flat surface may segment a right lobe of the liver in the scan image into an upper segment and a lower segment. The segmentation flat surface may be parallel to the cross section and pass through the RP point.

In 830, the segmentation surface determination unit 620 may determine one or more lines of intersection based on the one or more segmentation surfaces and the one or more cross sections. The one or more lines of intersection may be used to determine one or more segmentation curved surfaces. The line of intersection may be a line segment or a straight line.

In some embodiments, the segmentation surface determination unit 620 may determine a line of intersection based on two flat surfaces. The line of intersection determined based on two flat surfaces may be referred to as a first line of intersection. In some embodiments, the first line of intersection may be determined based on a segmentation flat surface and a cross section passing through a point on the segmentation flat surface. The determined first line of intersection may pass through the point on the segmentation flat surface. For example, a first line of intersection may be determined by a segmentation flat surface determined by a P point, a V point, and an MV point, and a cross section passing through the MV point. As another example, a first line of intersection may be determined based on a segmentation flat surface determined by a P point, a V point, and an RV point, and a cross section passing through the RV point. As still another example, a first line of intersection may be determined based on a segmentation flat surface determined by a P point, a V point, an LF point, and an LP point, and a cross section passing through the LF point.

In some embodiments, the segmentation surface determination unit 620 may determine a line of intersection based on an algorithm. The line of intersection determined based on an algorithm may be referred to as a second line of intersection. In some embodiments, the segmentation surface determination unit 620 may determine one or more second lines of intersection based on one or more first lines of intersection and an interpolation algorithm. A continuous and smooth curved surface may be determined based on the one or more first lines of intersection and the one or more second lines of intersection. The interpolation algorithm may include but is not limited to an interpolation algorithm based on distance field. For example, the marked point determination unit 610 may determine a P point, a V point, and ten MV points (e.g., $MV_1, MV_2, \ldots, MV_{10}$). A segmentation flat surface (e.g., $P_1, P_2, \ldots, P_{10}$) may be determined based on one of the ten MV points, the P point, and the V point. A first line of intersection (e.g., $L_{A1}, L_{A2}, \ldots, L_{A10}$) may be determined based on a segmentation flat surface and a cross section that passes through the MV point on the segmentation flat surface. The segmentation surface determination unit 620 may determine one or more second lines of intersection based on the ten first lines of intersection and an interpolation algorithm. The segmentation surface determination unit 620 may determine a continuous segmentation curved surface that segments the liver in the scan image into a left lobe and a right lobe based on the one or more second lines of intersection and the ten first lines of intersection.

In 840, the segmentation surface determination unit 620 may determine one or more segmentation curved surfaces based on the one or more lines of intersection. In some embodiments, the segmentation surface determination unit 620 may determine one or more continuous segmentation curved surfaces based on the one or more lines of intersection (including one or more first lines of intersection and one or more second lines of intersection) determined in 830. For example, a continuous segmentation curved surface may be determined based on first lines of intersection determined by a P point, a V point, and a plurality of MV points, and second lines of intersection. The segmentation curved surface may pass through the plurality of MV points and segment the liver in the scan image into a left lobe and a right lobe.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, in some embodiments, 810 may be performed after 820. Alternatively, 810 and 820 may be performed simultaneously. As another example, in some embodiments, after 840, an operation of processing (e.g., smoothing or deforming) the one or more segmentation curved surfaces may be added. As still another example, in some embodiments, after 840, an operation of displaying the segmentation result may be added.

Figure 9:
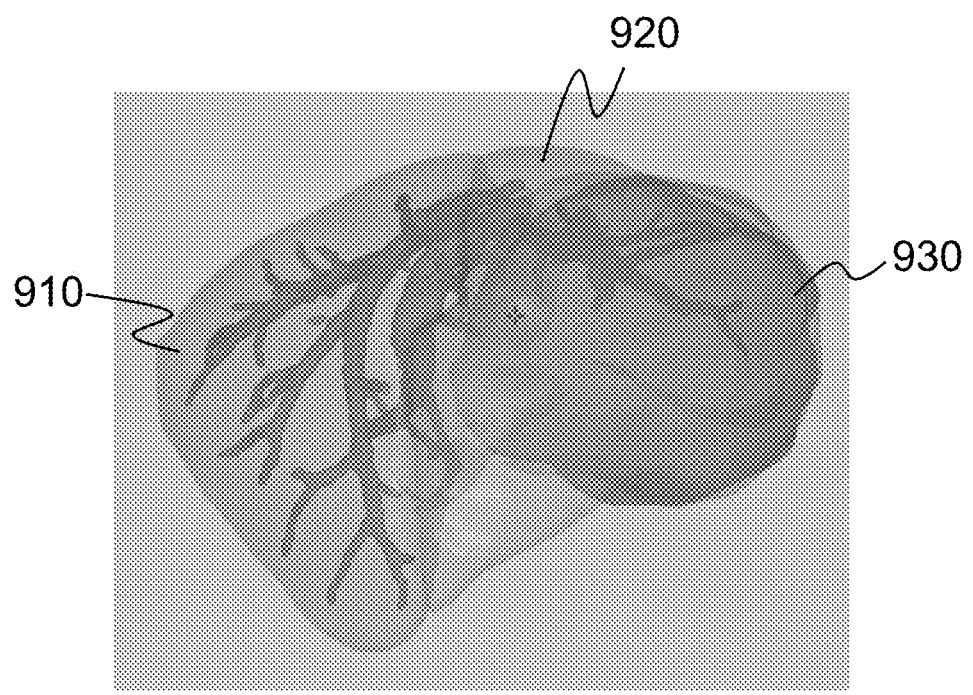
FIG. 9 is a schematic diagram illustrating an exemplary segmentation result of a liver in a scan image according to some embodiments of the present disclosure.

FIG. 9 is a schematic diagram illustrating an exemplary segmentation result of a liver in a scan image according to some embodiments of the present disclosure. The segmentation result illustrated in FIG. 9 corresponds to a segmentation protocol of the segmentation relating to the hepatic left lobe and the hepatic right lobe. As shows in FIG. 9, a liver in the image is segmented into a left lobe (including 910 and 920) and a right lobe 920 by a continuous segmentation curved surface using the method for determining liver segments described in the present disclosure.

FIGS. 10-A to 10-D are schematic diagrams illustrating exemplary segmentation results of a liver in a scan image according to some embodiments of the present disclosure. The segmentation results of FIGS. 10-A to 10-D correspond to a segmentation protocol of the segmentation relating to the hepatic seven segments. FIGS. 10-A to 10-C are 2D CT scan images of a liver. The location, in the liver, of the section of the liver displayed in each of FIGS. 10-A to 10-C is shown in the lower right corner of FIGS. 10-A to 10-C, respectively. FIG. 10-A is a 2D CT scan image of a cross section of the liver. The cross section of the liver passes through the white line shown in FIG. 10-A. FIG. 10-B is a 2D CT scan image of a cross section of the liver. The cross section of the liver passes through the white line shown in FIG. 10-B. FIG. 10-C is a 2D CT scan image of a coronal plane of the liver. The coronal plane passes through the white line shown in FIG. 10-C. FIG. 10-D is a 3D image of the liver reconstructed based on one or more 2D CT scan images of the liver.

As shown in FIGS. 10-A to 10-D, the segmentation result may be displayed on a 2D CT scan image or a 3D image. As shown in FIG.10-A, 1011 refers to an upper segment of a right posterior lobe (liver segment 7), 1012 refers to an upper segment of a right anterior lobe (liver segment 8), 1015 refers to a left medial lobe (liver segment 4), and 1013 refers to an upper segment of a left lateral lobe (liver segment 2). As shown in FIG.10-B, 1014 refers to a lower segment of the right posterior lobe (liver segment 5), and 1016 refers to a lower segment of the right anterior lobe (liver segment 6). As shown in FIG.10-C, 1017 refers to a lower segment of the left lateral lobe (liver segment 3).

Figure 11:
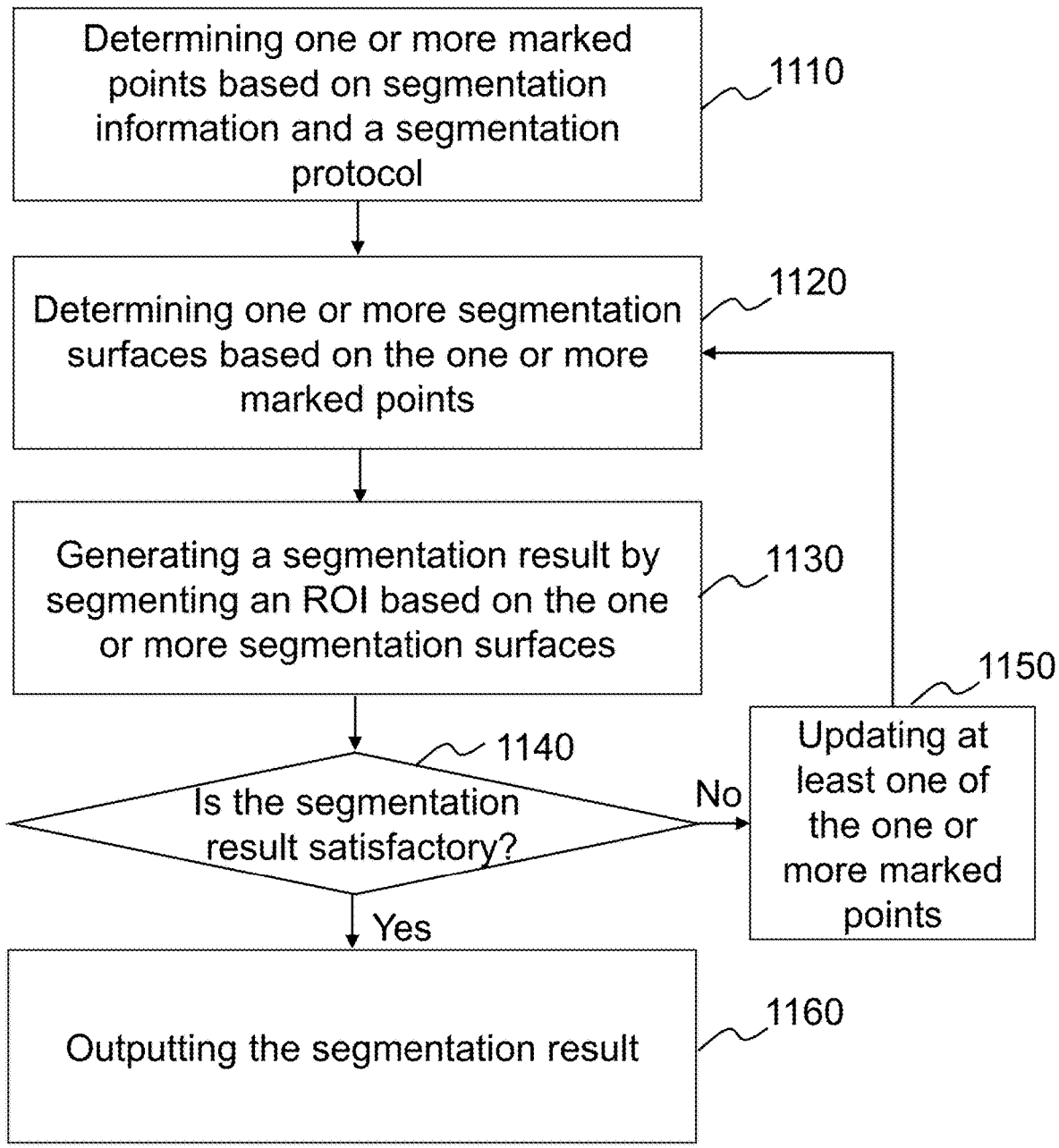
FIG. 11 is a flowchart illustrating an exemplary process for segmenting an ROI according to some embodiments of the present disclosure.

FIG. 11 is a flowchart illustrating an exemplary process for segmenting an ROI according to some embodiments of the present disclosure. In some embodiments, when a user (e.g., a doctor, an imaging technician) is not satisfied with the segmentation surfaces determined by the processing device 130 automatically, the user may manually adjust at least one marked point and/or at least one segmentation surface through the I/O device of the processing device 130 to generate a segmentation result satisfactory to the user.

In 1110, the marked point determination unit 610 may determine one or more marked points based on segmentation information and a segmentation protocol.

In 1120, the segmentation surface determination unit 620 may determine one or more segmentation surfaces based on the one or more marked points.

In 1130, the segmentation result generation unit 630 may generate a segmentation result by segmenting an ROI in a scan image based on the one or more segmentation surfaces.

In 1140, the segmentation result generation unit 630 may determine whether the segmentation result is satisfactory to a user based on an instruction obtained from the user. If the user is satisfied with the segmentation result, the process 1100 may proceed to 1160. The segmentation result generation unit 630 may output the segmentation result generated in 1130 as a final result. If the user is not satisfied with the segmentation result, the process 1100 may proceed to 1150. The user may manually adjust at least one of the one or more marked points (e.g., add one or more new marked points, delete at least one of the one or more marked points, change the location of at least one of the one or more marked points) by the I/O device of the processing device 130. After receiving an instruction relating to adjusting at least one of the one or more marked points, the marked point determination unit 610 may update the one or more marked points based on the instruction. The segmentation surface determination unit 620 may determine one or more segmentation surfaces based on the updated marked points determined by the marked point determination unit 610, until a segmentation result that is satisfactory to the user is generated.

In some embodiments, after generating a segmentation result, the segmentation result generation unit 630 may present the segmentation result to the user in a visual way through the I/O device and send an instruction to the I/O device to determine whether the user is satisfied with the segmentation result. The user (e.g., a doctors or an imaging technician) may input an instruction (e.g., click a dialog box of "satisfied" or "dissatisfied", or a dialog box of "confirmation" or "editing") as to whether to be satisfied with the segmentation result through the I/O device.

In some embodiments, after the marked point determination unit 610 determines the one or more marked points, the one or more marked points may be presented in a visual way to a user through the I/O device. The marked point determination unit 610 may send an instruction to the I/O device to determine whether the user is satisfied with the one or more marked points. If the user is satisfied with the one or more marked points, the segmentation surface determination unit 620 may determine one or more segmentation surfaces based on the one or more marked points. If the user is not satisfied with the one or more marked points, the user may manually adjust at least one of the one or more marked points (e.g., add one or more new marked points, delete at least one of the one or more marked points, change the location of at least one of the one or more marked points).

In some embodiments, after the segmentation surface determination unit 620 determines the one or more segmentation surfaces, the one or more segmentation surfaces may be presented in a visual way to a user through the I/O device. The segmentation surface determination unit 620 may send an instruction to the I/O device to determine whether the user is satisfied with the one or more segmentation surfaces. If the user is satisfied with the one or more segmentation surfaces, the segmentation result generation unit 630 may generate a segmentation result based on the one or more segmentation surfaces. If the user is not satisfied with the one or more segmentation surfaces, the user may manually adjust at least one of the one or more segmentation surfaces (e.g., add one or more new segmentation surfaces, delete at least one of the one or more segmentation surfaces, change the angle, the location, or the size of at least one of the one or more segmentation surfaces).

Figure 12:
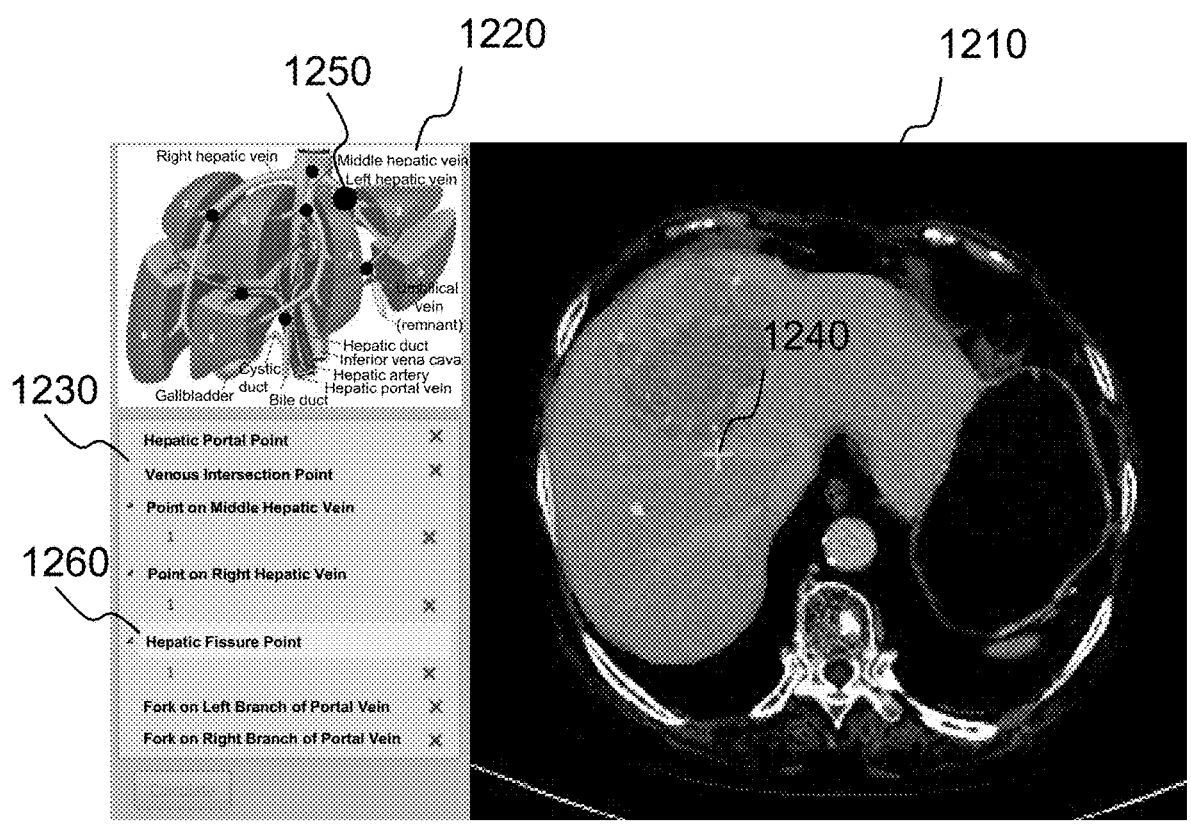
FIG. 12 is a schematic diagram illustrating an interface for adjusting one or more marked points by a user according to some embodiments of the present disclosure.

FIG. 12 is a schematic diagram illustrating an interface for adjusting one or more marked points by a user according to some embodiments of the present disclosure. In some embodiments, a user may adjust at least one of the one or more marked points (e.g., add one or more new marked points, delete at least one of the one or more marked points, change at least one of the one or more marked points) in a display interface of the I/O device. In some embodiments, the user may adjust the at least one of the one or more marked points on a 2D scan images including a section of a liver or a 3D image of the liver. For the 2D CT scan image of a liver, as shown in FIG.12, the display interface may include but is not limited to a 2D CT scan image 1210 of a liver, a liver 3D model 1220, and a description column 1230 of marked point. The user may adjust at least one of the one or more marked points on the 2D CT scan image 1210. One or more points displayed in the liver 3D model 1220 may correspond to the one or more marked points in the 2D CT scan image 1210. The names and the numbers of the one or more marked points may be displayed in the description column 1230 of marked point. The one or more corresponding points displayed in the liver 3D model 1220, and the names and the numbers of the one or more marked points displayed in the description column 1230 may be changed according to the adjustment of at least one of the one or more marked points in the 2D CT scan image 1210. For example, when the user selects an LF point 1240 in the 2D CT scan image 1210, a point 1250 corresponding to the LF point 1240 in the liver 3D model 1220 may be highlighted (e.g., the color of the point 1250 may be transformed, the point 1250 may be zoomed or flickering). The name 1260 of the LF point 1240 may be highlighted (e.g., the color of the name 1260 may be transformed, the name 1260 may be zoomed or flickering) in the description column 1230. As another example, when the user deletes a marked point in the 2D CT scan image 1210, the corresponding point in the liver 3D model 1220 may disappear. The number of the deleted marked points in the description column 1230 may by subtracted by one. In some embodiments, a 2D scan image of a liver may display a certain section of the liver and may not display the whole liver. The user may adjust at least one of the one or more marked points in different 2D scan images of different sections of the liver.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:

1. A method for determining liver segments in a medical image implemented on a computing device having one or more processors and one or more storage devices, the method comprising:
   obtaining a scan image of a target object, the target object including at least part of a liver;
   obtaining a segmentation protocol;
   obtaining segmentation information associated with the scan image;
   determining a plurality of marked points based on the segmentation information and the segmentation protocol;
   determining one or more segmentation curved surfaces based on the plurality of marked points, including:
      determining a plurality of segmentation flat surfaces based on the plurality of marked points;
      obtaining, based on the scan image, a plurality of cross sections corresponding to the plurality of segmentation flat surfaces;
      determining lines of intersection based on the plurality of segmentation flat surfaces and the plurality of cross sections;
      determining the one or more segmentation curved surfaces based on the lines of intersection, the one or more segmentation curved surfaces being configured to segment the at least part of the liver into a plurality of liver segments; and
   determining a segmentation result of the at least part of the liver in the scan image based on the one or more segmentation curved surfaces.

2. The method of claim 1, wherein the segmentation information includes at least one of image grayscale information, image structure information, structure information of the target object, and blood vessel information of the target object.

3. The method of claim 1, wherein the segmentation protocol includes at least one of segmentation relating to a hepatic left lobe and a hepatic right lobe, segmentation relating to hepatic left three lobes, segmentation relating to hepatic right three lobes, segmentation relating to a hepatic middle lobe, segmentation relating to an upper segment and a lower segment of the hepatic right lobe, segmentation relating to hepatic four lobes, segmentation relating to hepatic five segments, segmentation relating to hepatic six segments, segmentation relating to hepatic seven segments, or segmentation relating to hepatic eight segments.

4. The method of claim 3, wherein the plurality of marked points include at least one of a point on a hepatic portal, a venous intersection point, a point on a middle hepatic vein, a point on a right hepatic vein, a hepatic fissure point, a fork on a left branch of a portal vein, a fork on a right branch of a portal vein, or a small hepatic fissure point of liver left lobe.

5. The method of claim 4, wherein the determining of the plurality of marked points based on the segmentation information and the segmentation protocol includes:
   for the segmentation relating to the hepatic left lobe and the hepatic right lobe, determining the point on the hepatic portal, the venous intersection point, and the point on the middle hepatic vein;
   for the segmentation relating to the hepatic left three lobes, determining at least one of the point on the hepatic portal, the venous intersection point, the point on the right hepatic vein, or the point on the middle hepatic vein;
   for the segmentation relating to the hepatic right three lobes, determining at least one of the point on the hepatic portal, the venous intersection point, the hepatic fissure point, the fork on the left branch of the portal vein, or the point on the middle hepatic vein;
   for the segmentation relating to the hepatic middle lobe, determining at least one of the point on the hepatic portal, the venous intersection point, the hepatic fissure point, the fork on the left branch of the portal vein, the point on the right hepatic vein, or the point on the middle hepatic vein;
   for the segmentation relating to the upper segment and the lower segment of the hepatic right lobe, determining the point on the hepatic portal, the venous intersection point, the fork on the right branch of the portal vein, and the point on the middle hepatic vein;
   for the segmentation relating to the hepatic four lobes, determining the point on the hepatic portal, the venous intersection point, the hepatic fissure point, the fork on the left branch of the portal vein, the point on the right hepatic vein, and the point on the middle hepatic vein;
   for the segmentation relating to the hepatic five segments, determining the point on the hepatic portal, the venous intersection point, the hepatic fissure point, the fork on the left branch of the portal vein, the point on the right hepatic vein, and the point on the middle hepatic vein;
   for the segmentation relating to the hepatic six segments, determining the point on the hepatic portal, the venous intersection point, the hepatic fissure point, the fork on the left branch of the portal vein, the point on the right hepatic vein, the fork on the right branch of the portal vein, and the point on the middle hepatic vein;
   for the segmentation relating to the hepatic seven segments, determining the point on the hepatic portal, the venous intersection point, the hepatic fissure point, the fork on the left branch of the portal vein, the point on the right hepatic vein, the fork on the right branch of the portal vein, and the point on the middle hepatic vein; and
   for the segmentation relating to the hepatic eight segments, determining the point on the hepatic portal, the venous intersection point, the hepatic fissure point, the fork on the left branch of the portal vein, the point on the right hepatic vein, the fork on the right branch of the portal vein, the point on the middle hepatic vein, and the small hepatic fissure point of the hepatic left lobe.

6. The method of claim 1, wherein the determining of the one or more plurality of marked points based on the segmentation information and the segmentation protocol includes:
   determining one or more candidate marked points based on the segmentation information and the segmentation protocol;
   obtaining a user instruction, the user instruction including at least one of adjusting the position of the one or more candidate marked points and deleting at least one of the one or more candidate marked points; and
   determining the plurality of marked points based on the user instruction and the one or more candidate marked points.

7. The method of claim 1, wherein the determining of the lines of intersection includes:
   determining first lines of intersection based on the plurality of segmentation flat surfaces and the plurality of cross sections; and
   determining second lines of intersection based on the first lines of intersection using an interpolation algorithm.

8. The method of claim 7, wherein the one or more segmentation curved surfaces are continuous and smooth, and the interpolation algorithm is based on distance field.

9. The method of claim 1, further comprising:
   determining a liver surgery plan based on the segmentation result of the at least part of the liver in the scan image.

10. The method of claim 1, wherein the determining of the plurality of marked points includes determining the plurality of marked points based on a vascular tracking algorithm.

11. The method of claim 1, wherein the plurality of marked points are determined automatically.

12. A method for determining liver segments in a medical image implemented on a computing device having at least one processor and at least one storage device, the method comprising:
   obtaining a scan image;
   obtaining a segmentation protocol;
   determining at least part of a liver and blood vessel information associated with the scan image by automatically segmenting the scan image based on the segmentation protocol;
   automatically determining a plurality of marked points on the liver based on the blood vessel information;
   automatically determining one or more segmentation curved surfaces based on the plurality of marked points, including:
      determining a plurality of segmentation flat surfaces based on the plurality of marked points;
      obtaining, based on the scan image, a plurality of cross sections corresponding to the plurality of segmentation flat surfaces;
      determining lines of intersection based on the plurality of segmentation flat surfaces and the plurality of cross sections; and
      determining the one or more segmentation curved surfaces based on the lines of intersection, the one or more segmentation curved surfaces being configured to segment the at least part of the liver into a plurality of liver segments; and
   determining a segmentation result of the at least part of the liver in the scan image by segmenting the at least part of the liver based on the one or more segmentation curved surfaces.

13. A device for determining liver segments in a medical image, comprising:
   at least one storage device including a set of instructions;
   at least one processor in communication with the at least one storage device, wherein when executing the set of instructions, the at least one processor is directed to cause the system to perform operations including:

obtaining a scan image of a target object, the target object including at least part of a liver;

obtaining a segmentation protocol;

obtaining segmentation information associated with the scan image;

determining a plurality of marked points based on the segmentation information and the segmentation protocol;

determining one or more segmentation curved surfaces based on the plurality of marked points, wherein the at least one processor is further directed to cause the system to perform operations including:

determining a plurality of segmentation flat surfaces based on the plurality of marked points;

obtaining, based on the scan image, a plurality of cross sections corresponding to the plurality of segmentation flat surfaces;

determining lines of intersection based on the plurality of segmentation flat surfaces and the plurality of cross sections; and determining the one or more segmentation curved surfaces based on the lines of intersection, the one or more segmentation curved surfaces being configured to segment the at least part of the liver into a plurality of liver segments; and determining a segmentation result of the at least part of the liver in the scan image based on the one or more segmentation curved surfaces.

14. The device of claim 13, wherein the segmentation information includes at least one of image grayscale information, image structure information, structure information of the target object, and blood vessel information of the target object.

15. The device of claim 13, wherein the segmentation protocol includes at least one of segmentation relating to a hepatic left lobe and a hepatic right lobe, segmentation relating to hepatic left three lobes, segmentation relating to hepatic right three lobes, segmentation relating to a hepatic middle lobe, segmentation relating to an upper segment and a lower segment of the hepatic right lobe, segmentation relating to the hepatic four lobes, segmentation relating to hepatic five segments, segmentation relating to hepatic six segments, segmentation relating to hepatic seven segments, or segmentation relating to hepatic eight segments.

16. The device of claim 15, wherein the plurality of marked points include at least one of a point on a hepatic portal, a venous intersection point, a point on a middle hepatic vein, a point on a right hepatic vein, a hepatic fissure point, a fork on a left branch of a portal vein, a fork on a right branch of a portal vein, or a small hepatic fissure point of liver left lobe.

17. The device of claim 16, wherein to determine the plurality of marked points based on the segmentation information and the segmentation protocol, the at least one processor is directed to cause the system to perform additional operations including:

for the segmentation relating to the hepatic left lobe and the hepatic right lobe, determining the point on the hepatic portal, the venous intersection point, and the point on the middle hepatic vein;

for the segmentation relating to the hepatic left three lobes, determining at least one of the point on the hepatic portal, the venous intersection point, the point on the right hepatic vein, or the point on the middle hepatic vein;

for the segmentation relating to the hepatic right three lobes, determining at least one of the point on the hepatic portal, the venous intersection point, the hepatic fissure point, the fork on the left branch of the portal vein, or the point on the middle hepatic vein;

for the segmentation relating to the hepatic middle lobe, determining at least one of the point on the hepatic portal, the venous intersection point, the hepatic fissure point, the fork on the left branch of the portal vein, the point on the right hepatic vein, or the point on the middle hepatic vein;

for the segmentation relating to the upper segment and the lower segment of the hepatic right lobe, determining the point on the hepatic portal, the venous intersection point, the fork on the right branch of the portal vein, and the point on the middle hepatic vein;

for the segmentation relating to the hepatic four lobes, determining the point on the hepatic portal, the venous intersection point, the hepatic fissure point, the fork on the left branch of the portal vein, the point on the right hepatic vein, and the point on the middle hepatic vein;

for the segmentation relating to the hepatic five segments, determining the point on the hepatic portal, the venous intersection point, the hepatic fissure point, the fork on the left branch of the portal vein, the point on the right hepatic vein, and the point on the middle hepatic vein;

for the segmentation relating to the hepatic six segments, determining the point on the hepatic portal, the venous intersection point, the hepatic fissure point, the fork on the left branch of the portal vein, the point on the right hepatic vein, the fork on the right branch of the portal vein, and the point on the middle hepatic vein;

for the segmentation relating to the hepatic seven segments, determining the point on the hepatic portal, the venous intersection point, the hepatic fissure point, the fork on the left branch of the portal vein, the point on the right hepatic vein, the fork on the right branch of the portal vein, and the point on the middle hepatic vein; and for the segmentation relating to the hepatic eight segments, determining the point on the hepatic portal, the venous intersection point, the hepatic fissure point, the fork on the left branch of the portal vein, the point on the right hepatic vein, the fork on the right branch of the portal vein, the point on the middle hepatic vein, and the small hepatic fissure point of the hepatic left lobe.

18. The device of claim 13, wherein the plurality of marked points are determined based on a vascular tracking algorithm.

19. The device of claim 13, wherein to determine the plurality of marked points based on the segmentation information and the segmentation protocol, the at least one processor is directed to cause the system to perform additional operations including:

determining one or more candidate marked points based on the segmentation information and the segmentation protocol;

obtaining a user instruction, the user instruction including at least one of adjusting the position of the one or more candidate marked points, deleting at least one of the one or more candidate marked points, and adding one or more new candidate marked points; and determining the plurality of marked points based on the user instruction and the one or more candidate marked points.

20. The device of claim 13, wherein to determine the lines of intersection, the at least one processor is directed to cause the system to perform additional operations including:
    determining first lines of intersection based on the plurality of segmentation flat surfaces and the plurality of cross sections; and
    determining second lines of intersection based on the first lines of intersection using an interpolation algorithm.

* * * * *